United States Patent [19]
Cutler et al.

[11] Patent Number: 5,578,309
[45] Date of Patent: Nov. 26, 1996

[54] CANDIDA ALBICANS PHOSPHOMANNOPROTEIN ADHESION AS A VACCINE

[75] Inventors: Jim E. Cutler; Yongmoon Han, both of Bozeman, Mont.

[73] Assignee: The Research and Development Institute, Inc., Bozeman, Mont.

[21] Appl. No.: 483,558

[22] Filed: Jun. 7, 1995

Related U.S. Application Data

[63] Continuation-in-part of Ser. No. 247,972, May 23, 1994.
[51] Int. Cl.⁶ ...................................................... A61K 39/00
[52] U.S. Cl. ..................................... 424/274.1; 424/184.1
[58] Field of Search ............................. 424/274.1, 184.1, 424/9

[56] References Cited

U.S. PATENT DOCUMENTS

| | | |
|---|---|---|
| 4,310,514 | 1/1982 | Durette . |
| 4,315,913 | 2/1982 | Durette . |
| 4,323,560 | 4/1982 | Baschang et al. . |
| 4,368,190 | 1/1983 | Shen et al. . |
| 4,397,838 | 8/1983 | d'Hinterland et al. . |
| 4,678,748 | 7/1987 | Sutka et al. . |
| 4,732,763 | 3/1988 | Beck et al. .............................. 424/433 |
| 5,032,404 | 7/1991 | Lopez–Berenstein et al. . |
| 5,288,639 | 2/1994 | Burnie et al. . |

OTHER PUBLICATIONS

Cutler, J. E., et al., "Antigenic variability of *Candida albicans* cell surface." Curr. Top. Med. Mycol. 5:27–47; 1994.
Kanbe, T. et al., "Evidence that mannans of *Candida albicans* are responsible for adherence of yeast forms to spleen and lymph node tissue." Infect. Immun., 61:2578–2584; 1993.
Kobayashi, H., et al., "Structural study of cell wall phosphomannan of *Candida albicans* NIH B—792 (serotype B) strain, with special reference to 1H and 13C NMR analyses of acid—labile oligomannosyl residues." Arch. Biochem. Biophys., 278:195–204; 1990.
Li, R. K., et al., "chemical definition of an epitope/adhesin molecule on *Candida albicans*." J. Biol. Chem., 268:18293–18299; 1993.
Matthews, R., et al., "Acquired immunity to systemic candidiasis in immunodeficient mice: Role of antibody to heat–shock protein 90." J. Infect. Dis., 166:1193–1194; 1992.
Matthews, R. C., et al., "Autoantibody to heat–shock protein 90 can mediate protection against systemic candidosis." Immunol., 74:20–24; 1991.
Mourad, S., et al., "Active immunization of mice against *Candida albicans*." Proc. Soc. Exp. Biol. Med., 106:570–572; 1961.
Sieck et al., Protection against murine disseminated candidiasis mediated by a *C. albicans*–specific T–cell line. Infect. Immun. 61:3540–3543, 1993.
Scheld, W. M et al, Infect. & Immunity, Jun. 1983, pp. 950–955.
Kanbe, T et al. Infect. & Immunity, May 1994, pp. 1662–1668.
Matthews, R et al, Lancet, Jul. 30, 1988, pp. 263–265.
Klotz, S. A et al, Infection + Immunity, Oct. 1983, pp. 374–384.
Torosantucci et al, J Gen Microbiol, 1990, 136, pp. 1421–1428.

*Primary Examiner*—James C. Housel
*Assistant Examiner*—Ginny Allen Portner
*Attorney, Agent, or Firm*—Lowe, Price, LeBlanc & Becker

[57] ABSTRACT

A composition, pharamaceutical composition, vaccine and method for the treatment of disseminated candidiasis due to infection by *C. albicans*. The composition includes phosphomannoprotein which contains adhesins from *C. albicans*.

5 Claims, 14 Drawing Sheets

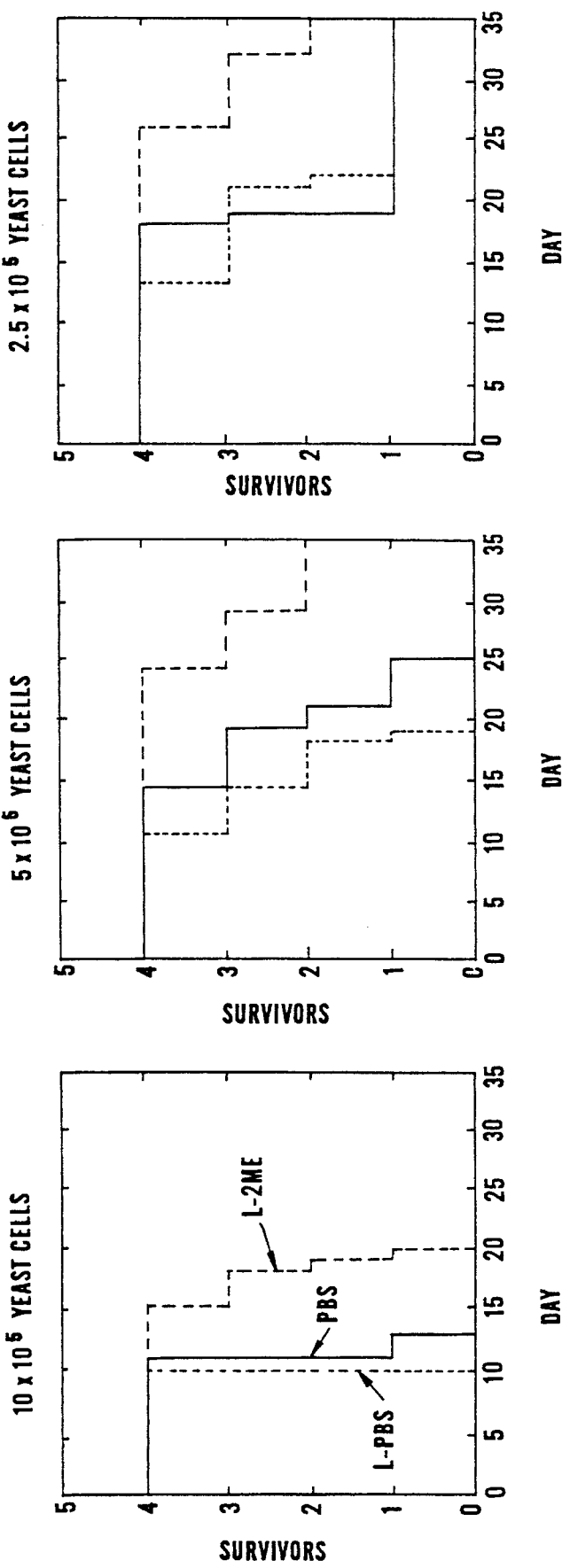

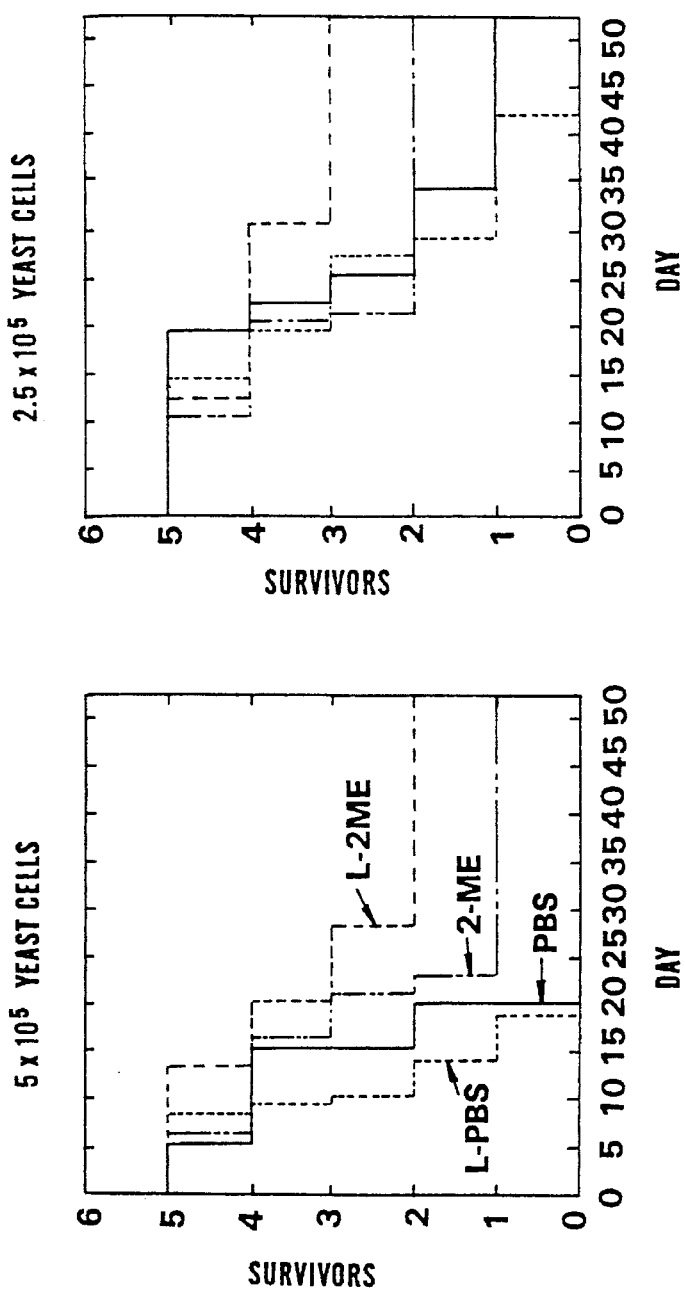

Vac-9  Effect of Active immunization

1. Survival mice up to 70 days by the active immunization were sacrificed and examined for yeast burden on kidneys.
2. The survival mice were:
   4/5 from L-2ME;
   2/5 from 2-me;
   2/5 from PBS treatments.
3. The mice had been challenged at $2.5 \times 10^5$/mouse.
4. No CFUs were determined from tested spleens.

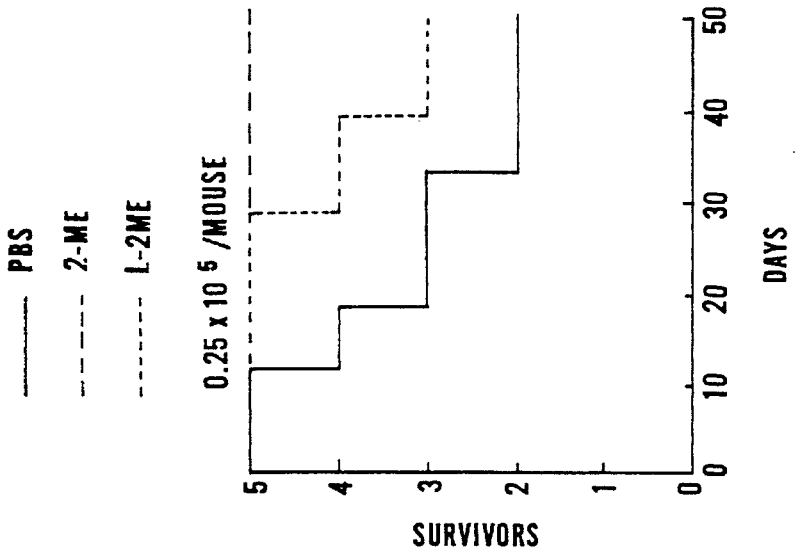
Figure 9A
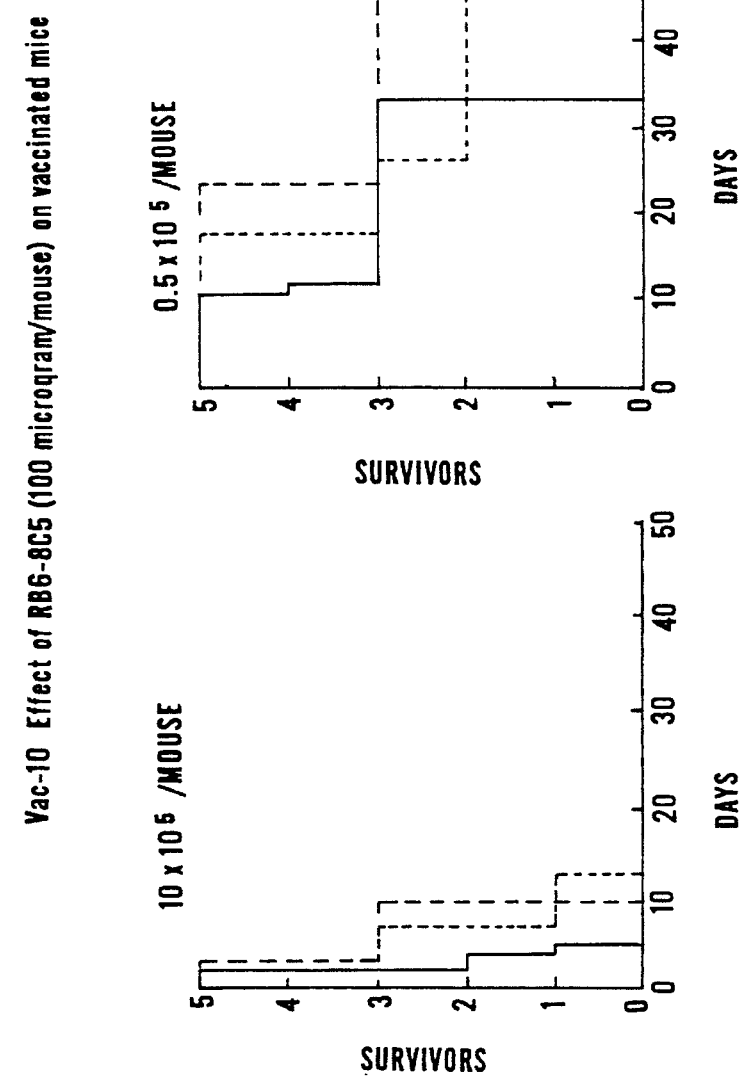
Figure 9B
Figure 9C

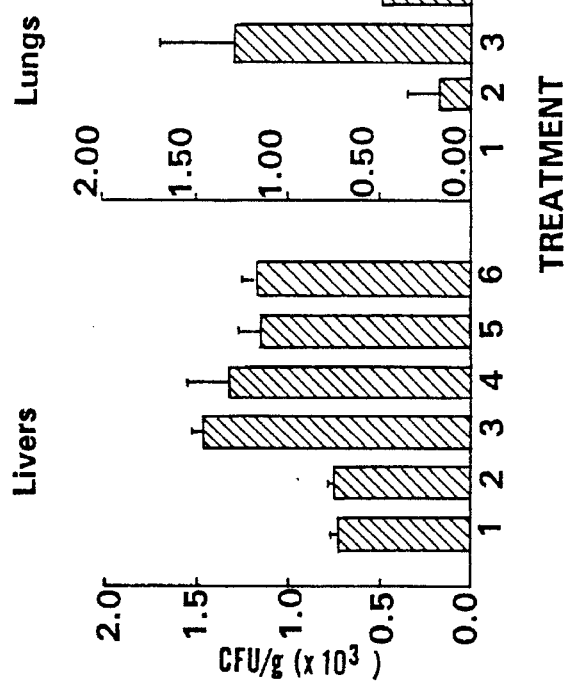
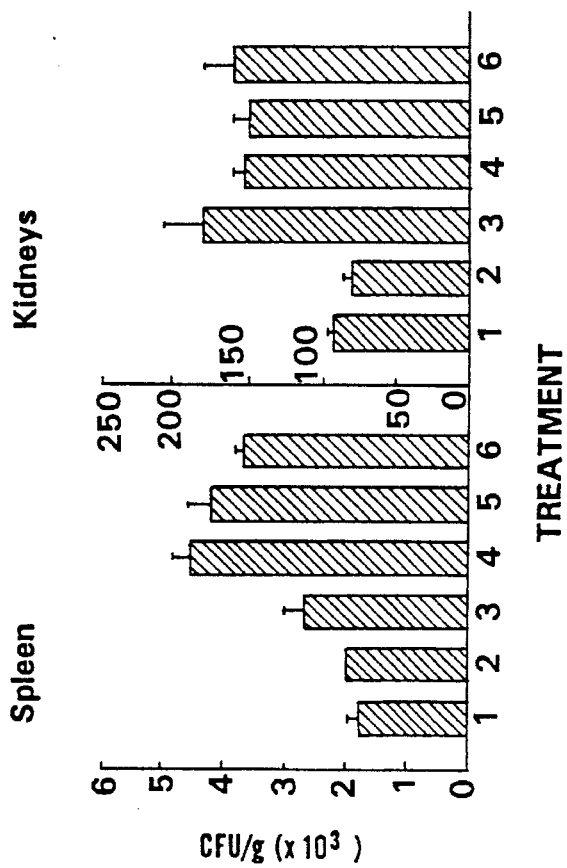
Figure 10A
Figure 10B
1. normal vaccine
2. heat-inactivated vaccine
3. adsorbed vaccine
4. heat-inactivated adsorbed vaccine
5. normal mouse serum
6. PBS

CANDIDA ALBICANS PHOSPHOMANNOPROTEIN ADHESION AS A VACCINE

This invention was made with United States Government support under Grant Numbers RO1 AI24912 and PO1 AI37194 awarded by the National Institutes of Health.

This application is a continuation-in-part of parent application Ser. No. 08/247,972 filed on May 23, 1994.

TECHNICAL FIELD

The present invention relates to a vaccine and method for the treatment of disseminated candidiasis due to infection by *Candida albicans*.

BACKGROUND OF THE INVENTION

*Candida albicans* is a fungus responsible for various forms of candidiasis, a condition which may be found in immunocompromised patients, such as those with acquired immune deficiency syndrome. Humans and mice who are neutropenic are especially at risk of developing disseminated candidiasis (Denning, D. W., et al. 1992. Antifungal prophylaxis during neutropenia or allogeneic bone marrow transplantation: what is the state of the art? Chemotherapy 38(suppl 1):43–49; Matsumoto, M. S., et al. 1991. Effect of combination therapy with recombinant human granulocyte colony-stimulating factor (rG-CSF) and antibiotics in neutropenic mice unresponsive to antibiotics alone. J. Antimicrob. Chemother. 28:447–453; Meunier, F. 1987. Prevention of mycoses in immunocompromised patients. Rev. Infect. Dis. 9:408–416; Meunier, F., et al. 1992. Candidemia in immunocompromised patients. Clin. Infect. Dis. 14 (Suppl 1):S120–S125; and Van't Wout, J. W. et al. 1989. Comparison of the efficacies of amphotericin B, Fluconazole, and Itraconazole against a systemic *Candida albicans* infection in normal and neutropenic mice. Antimicrob. Agents Chemother. 33: 147–151).

Several attempts have been made in the prior art to achieve immunostimulating compounds for the treatment of candidiasis as evidenced below.

U.S. Pat. No. 5,288,639 to Bernie et al. discloses the use of antibodies specific for stress proteins of *C. albicans* for the treatment of systemic candidiasis. Bernie et al. isolated a 47 kilo-dalton immunodominant antigen from *C. albicans* and found that serum from patients with systemic candidiasis reacts with the antigen. Monoclonal antibodies raised against the fungal stress proteins produced a 33% survival at 24 hours in animals challenged with a lethal dose of the *C. albicans*.

U.S. Pat. No. 4,397,838 to d'Hinterland discloses preparations of purified bacterial membranal proteoglycans. The proteoglycans serve as immuno-adjuvants and have an immunostimulating activity without being immunogenic themselves. The proteoglycans of the invention are extracted from membranes of bacteria. They are useful in serving as adjuvants with ribosomal vaccines such as a vaccine containing the ribosomes of *C. albicans*.

U.S. Pat. No. 4,310,514 to Durette et al. discloses immunologically active dipeptidyl 5-O,6-O-acyl-2-amino-2-deoxy-D-glucofuranose derivatives. The compounds are used to delay the release of an antigen and stimulate the immune response of the host in conjunction with a vaccine. Compounds of Durette provide non-specific host protection against infectious organisms such as *C. albicans*.

U.S. Pat. No. 4,315,913 to Durette discloses immunologically active dipeptidyl 2-amino-1,2-dideoxy-D-glucose derivatives. These derivatives are also useful as immunological adjuvants and themselves provide non-specific host protection against *C. albicans*.

U.S. Pat. No. 4,368,910 to Shen et al. is directed to immunologically active dipeptidyl 4-O-6-O-acyl-2-amino-2-deoxy-D-glucose derivatives. These derivatives are indicated to be useful as immunogenic agents and vaccines and by themselves provide non-specific host protection against infectious organisms such as *C. albicans*.

U.S. Pat. No. 4,323,560 to Baschang et al. is directed to phosphorylmuramyl peptides. The peptides are used to stimulate immunity. The compounds of Baschang et al. have been found to be inhibitive to infections of fungi such as *C. albicans*.

U.S. Pat. No. 5,032,404 to Lopez-Berestein et al. disclose a liposomal agent for treating disseminated fungal infection in an animal. Because of the nature of polysaccharide fungal cell walls, it is expected that all medically important fungi activate complement. The patent indicated that there is a positive correlation between animals deficient in late-acting complement components and increase of susceptibility to fungi such as *C. albicans*. The patent indicates that disseminated fungal infection can be treated with liposomal agent comprising lipids, a polyene macrolide anti-fungal compound and cholesterol. Lipids can include phosphatidyl choline. Liposomes incorporate an effective amount of a polyene macrolide anti-fungal compound such as hamycins or lucensomycin, filipin, lagosin and natamycin.

U.S. Pat. No. 4,678,748 to Sutka et al. discloses a process for the production of the immunobiological preparations applicable in the diagnosis, prevention and treatment of *Candida guilliermondii* infections. Strains of *C. guilliermondii* are killed and the attenuated fungus is used to formulate a vaccine.

Early attempts at obtaining compounds which provide non-specific host protection against *C. albicans* are generally in the form of immuno adjuvants used in conjunction with vaccines.

Discussion below provides an understanding of adherence as it relates to pathogenesis of disseminated candidiasis. *C. albicans* is an organism that may show considerable variability of certain characteristics. Genetics studies show that the organism is diploid, but apparently without the ability to undergo meiosis, yet it has impressive genetic variability between and within strains (Scherer, S. et al. 1990. Genetics of *C. albicans*. Microbiol. Rev. 54:226–241). Chromosomal aberrations unpredictably occur (Rustchenko-Bulgac et al. 1990. Chromosomal rearrangements associated with morphological mutants provide a means for genetic variation of *C. albicans*. J. Bacteriol, 172:1276–1283), and may be related to high frequency phenotypic (colony) changes in some strains (Soll, D. R. 1992. High-frequency switching in *C. albicans*. Clin. Microbiol. Rev. 5:183–203). Perhaps related to the genetic instability are findings that strains of *C. albicans* variably express cell surface antigens (Cutler, J. E., et al. 1994. Antigenic variability of *C. albicans* cell surface. Curr. Top. Med. Mycol. 5:27–47, and Martinez, J. P., et al. 1990. Wall mannoproteins in cells form colonial phenotypic variants of *C. albicans*. J. Gen. Microbiol. 136:2421–2432). Some of these antigens include putative virulence factors such as adhesins and enzymes (Cutler, J. E. 1991. Putative virulence factors of *C. albicans*. Ann. Rev. Microbiol. 45:187–218).

Studies on adherence properties of *C. albicans* are important in gaining an understanding of *C. albicans* interactions with its host. The ability to bind to mucus and epithelial surfaces likely plays a critical role in maintaining *C. albicans* at these locations. The fungus also shows adherence specificities for selected populations of splenic and lymph node macrophages (Cutler, J. E., et al. 1990. Characteristics of *C. albicans* adherence to mouse tissue. Infect. Immun. 58:1902–1908; Han, Y., et al. 1993. Binding of *C. albicans* yeast cells to mouse popliteal lymph node tissue is mediated by macrophages. Infect. Immun. 61:3244–3249; and Kanbe, T., et al. 1992. Evidence that *C. albicans* binds via a unique adhesion system on phagocytic cells in the marginal zone of the mouse spleen. Infect. Immun. 60:1972–1978), and extracellular matrix proteins (ECM) and endothelial cells (Filler, S. G., et al. 1991. *C. albicans* stimulates endothelial cell eicosanoid production. J. Infect. Dis. 164:928–035; Klotz, S. A. 1992. Fungal adherence to the vascular compartment: A critical step in the pathogenesis of disseminated candidiasis. Clin. Infect. Dis. 14:340–347; Mayer, C. L., et al. 1992. Technical report: *C. albicans* adherence to endothelial cells. Microvascular Res. 43:218–226; Rotrosen, D. et al. 1985. Adherence of Candida to cultured vascular endothelial cells: mechanisms of attachment and endothelial cell penetration. J. Infect. Dis. 153:1264–1274).

The fungal adhesins range in properties from hydrophilic to hydrophobic molecules (Hazen, K. C. 1990. Cell surface hydrophobicity of medically important fungi, especially Candida species, p. 249–295. In R. J. Doyle and M. Rosenberg (ed.), Microbial Cell Surface Hydrophobicity. American Society of Microbiology, Washington; Kennedy, M. J. 1988. Adhesion and association mechanisms of *C. albicans*. Curr. Top. Med. Mycol. 2:73–169) and all may be mannoproteins (8, 11). Both mannan and protein moieties may function as adhesins.

Some adhesins have integrin-like activity in that they act as receptors for mammalian proteins such as iC3b, fibronectin, laminin and fibrinogen; one adhesin has lectin-like activity; and a C3d receptor has been described (Bendel, C. M., et al. 1993. Distinct mechanisms of epithelial adhesion for *C. albicans* and *Candida tropicalis*. Identification of the participating ligands and development of inhibitory peptides. J. Clin. Invest. 92:1840–18492; Calderone, R. A., et al. 1991. Adherence and receptor relationships in *C. albicans*. Microbiol. Rev. 55:1–20; Cutler, J. E. 1991. Putative virulence factors of *C. albicans*. Ann. Rev. Microbiol. 45:187–218; Gilmore, B. J., et al. 1988 An iC3b receptor on *C. albicans*: structure, function, and correlates for pathogenicity. J. Infect. Dis. 157:38–46; Klotz, S. A., et al. 1993. Adherence of Candida to immobilized extracellular matrix proteins is mediated by *C. albicans* calcium-dependent surface glycoproteins. Microbial 14:133–147. Pathogens is the surface of hydrophilic yeast cells of *C. albicans* has a fibrillar appearance both in vitro and in vivo (Hazen, K. C. et al. 1993. Surface hydrophobic and hydrophilic protein alterations in *C. albicans*. FEMS Microbiol. Lett. 107:83–88; Marrie, T. J., et al. 1981. The ultrastructure of *C. albicans* infections. Can. J. Microbiol. 27:1156–1164; and Tokunaga, M. et al. 1986. Ultrastructure of outermost layer of cell wall in *C. albicans* observed by rapid-freezing technique, J. Electron Microsc. 35:237–246).

A major component that makes up the fibrils on the cell surface of *C. albicans* and extends deeper into the cell surface appears to be the phosphomannoprotein (PMP) as depicted in the simplistic diagram presented as FIG. 1. The cell surface is probably more complex than this, as additional proteins with relatively small amounts of carbohydrate may also be present (Hazen, K. C., et al. 1994. Hydrophobic cell wall protein glycosylation by the pathogenic fungus *C. albicans*. Can. J. Microbiol. 40:266–272). It is not clear, however, if these proteins differ from the major PMP or are the same proteins, but with a truncated version of the glycan portion.

The present inventors have overcome the deficiencies and inability of the prior art to obtain a vaccine against disseminated candidiasis by directing their attention to a composition comprising *C. albicans* adhesins.

DISCLOSURE OF THE INVENTION

Accordingly, an object of the present invention is to provide a vaccine against disseminated candidiasis by incorporating part, or all, of the *C. albicans* PMP into liposomes.

A further object of the invention is to provide a method of preventing and treating disseminated candidiasis by passive transfer to a host of antibodies specific for the PMP.

This object involves passive transfer of immune sera from vaccinated animals, mAbs specific for the PMP of *C. albicans*, and mAbs specific for hydrophobic proteins of *C. albicans*. The antibodies may be given prior (prophylaxis or prevention) to or after (treatment) infection of a host with *C. albicans*.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

Statement of Deposit

Monoclonal Antibody B6.1 (930610) was deposited under the terms of the Budapest Treaty on Jun. 7, 1995 with the American Type Culture Collection, 12301 Parklawn Drive, Rockville, Md., U.S.A.

BRIEF DESCRIPTION OF THE FIGURES

FIGS. 4A–4C show the protective or prophylactic effect of the liposome-2ME extract (L-2ME) as a vaccine against disseminated candidiasis. Mice were vaccinated with the L-2ME, with liposomes alone (L-PBS) or buffer alone (PBS), then challenged i.v. with various doses of *C. albicans*.

FIGS. 5A and 5B show a therapeutic effect of the liposome 2 ME extract (L-2ME) vaccine. Mice infected with *C. albicans* and then vaccinated survived longer than control animals.

FIGS. 9A–9C show that neutropenic mice may also be protected by the vaccine. Mice were vaccinated, then made neutropenic and challenged i.v. with *C. albicans*. The vaccinated mice tended to survive longer than control neutropenic mice.

FIGS. 10A and 10B show a confirmation experiment of the experimental results shown in FIGS. 6 and 8 which imply that antibody is responsible for the protective effect of serum from vaccinated mice. Heat treatment (56° C., 20 min.) did not remove the protective value of immune serum, but the protective value was removed by adsorption of the serum with *C. albicans* yeast cells.

DESCRIPTION OF THE INVENTION

Figure 1:
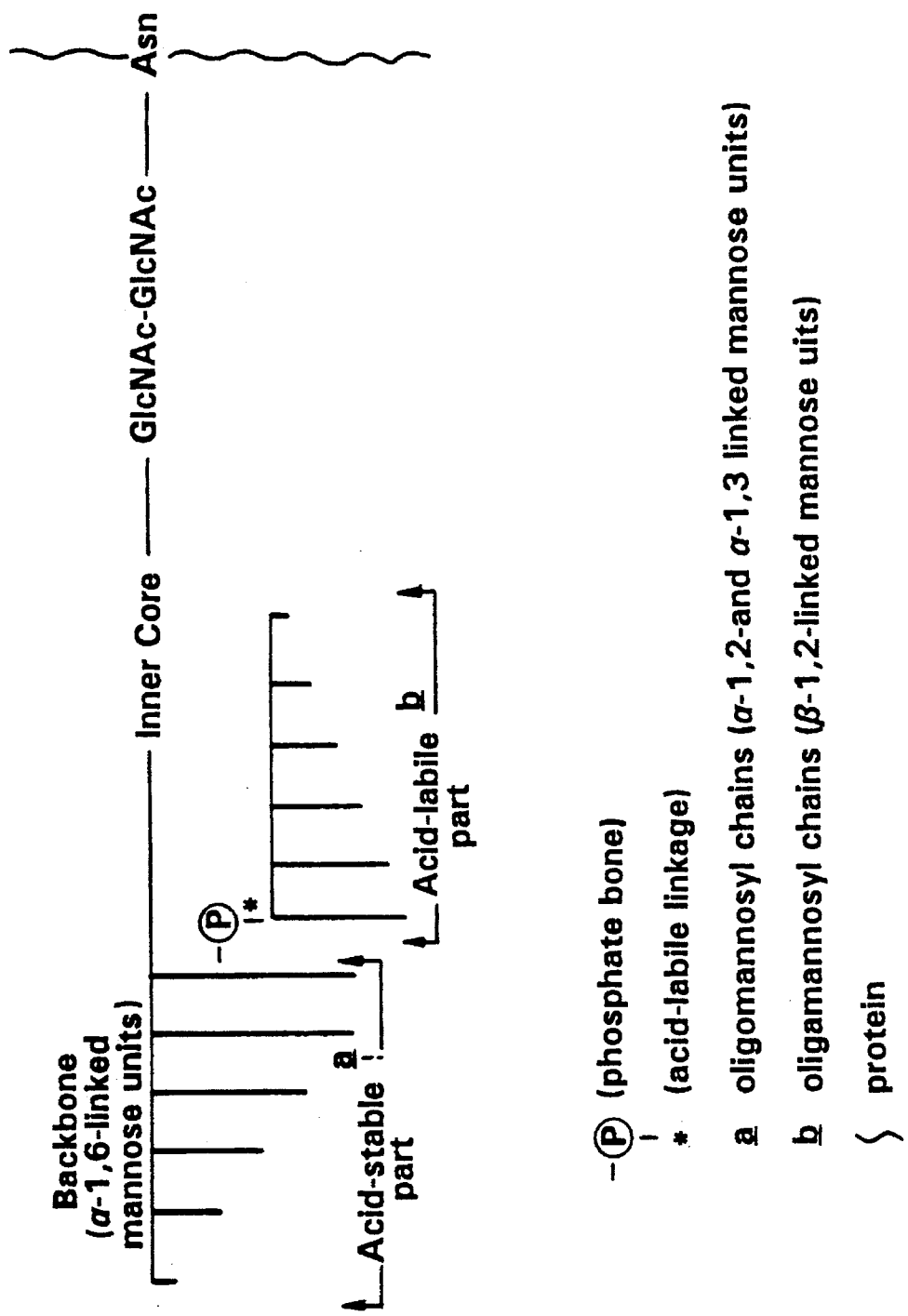
FIG. 1 shows a model of the phosphomannoprotein (PMP) complex surface of *C. albicans*. The PMP contains the adhesins responsible for *C. albicans* yeast cell adherence to mouse macrophages located in splenic marginal zones and in particular regions of peripheral lymph nodes.

This invention investigates a vaccine induced alteration of pathogenesis of candidiasis, particularly hematogenous disseminated candidiasis. The invention focuses on optimizing a vaccine against candidal adhesins and determining the effect of immune serum on its ability to protect mice against disseminated candidiasis.

Data of the invention indicates that i) immune responses against candidal phosphomannoprotein moieties protect mice against disseminated candidiasis, (ii) sera from immune animals transfer protection to naive mice.

The underlying emphasis of studies leading to the present invention was to determine the role of adhesin-specific antibodies in host resistance to disseminated candidiasis and define the effects of these antibodies on fungal attachment phenomena as measured by several in vitro adherence systems, and by in vivo analysis. The invention focuses on the phosphomannoprotein complex which the inventors have shown to contain adhesin sites.

The adhesin(s) responsible for adherence of *C. albicans* hydrophilic yeast cells to the splenic marginal zone was isolated, and presentation of the adhesin (as part of the phosphomannoprotein complex) to mice resulted in induction of specific antibody responses. Mice were induced to produce polyclonal antisera specific for the phosphomannoprotein and a few mAbs have been isolated. Mice who develop anti-phosphomannoprotein responses show increased survival against disseminated candidiasis. Sera from vaccinated mice specifically react with phosphomannoprotein. Immune serum has been shown to passively transfer resistance to naive animals. The invention addresses the role of antibodies in host defense against disseminated candidiasis.

An understanding of mechanisms by which blood-borne *C. albicans* yeast cells disseminate in the host may be gained through knowledge of fungal adhesins and host ligand molecules to which these adhesins bind. The findings by Klotz and others that *C. albicans* attaches to exposed basement membrane (ECM) and platelet aggregates on the ECM, led to speculation that damaged endothelial cells expose the ECM and allow attachment of *C. albicans* from the circulatory system (Klotz, S. A. 1992. Fungal adherence to the vascular compartment: A critical step in the pathogenesis of disseminated candidiasis. Clin. Infect. Dis. 14:340–347). Perhaps relevant to these findings is that indwelling venous catheters are responsible for increased susceptibility to candidiasis and it is believed that venous catheters damage endothelia. Importantly, the kidney is a target organ for systemic disease and this organ normally has an exposed basement membrane (ECM) as part of the glomerular apparatus. Edwards has demonstrated that *C. albicans* binds directly to the endothelial cells (Filler, S. G., et al. 1987. An enzyme-linked immunosorbent assay for quantifying adherence of Candida to human vascular endothelium. J. Infect. Dis. 156:561–566; and Rotrosen, D. et al. 1985. Adherence of Candida to cultured vascular endothelial cella: mechanisms of attachment and endothelial cell penetration. J. Infect. Dis. 153:1264–1274), and this event may well initiate host inflammatory changes (Filler, S. G., et al. 1994. Mechanisms by which *C. albicans* induces endothelial cell prostaglandin synthesis. Infect. Immun. 62:1064–1069; and Filler, S. G., et al. 1991. *C. albicans* stimulates endothelial cell eicosanoid production. J. Infect. Dis. 164:928–035). A shear dependent adherence assay has allowed observations that corroborate some of the endothelial binding interactions.

The adherence of *C. albicans* hydrophilic yeast cells to mouse splenic marginal zone macrophages and macrophages within the subcapsular and medullary sinuses of peripheral lymph nodes has been characterized by the present inventors (Cutler, J. E., et al. 1990. Characteristics of *C. albicans* adherence to mouse tissue. Infect. Immun. 58:1902–1908; Han, Y., et al. 1993. Binding of *C. albicans* yeast cells to mouse popliteal lymph node tissue is mediated by macrophages. Infect. Immun. 61:3244–3249; Hazen, K. C., et al. 1991. Differential adherence between hydrophobic and hydrophilic yeast cells of *C. albicans*. Infect. Immun. 59:907–912; and Kanbe, T., et al. 1992. Evidence that *C. albicans* binds via a unique adhesion system on phagocytic cells in the marginal zone of the mouse spleen. Infect. Immun. (60:1972–1977)).

The adhesins responsible for the yeast/macrophage interaction have been isolated and characterized (Kanbe, T., et. al. 1994. Evidence for adhesin activity in the acid-stable moiety of the phosphomannoprotein cell wall complex of *C. albicans*. Infect. Immun. 62:1662–1668); and Kanbe, T., et al. 1993. Evidence that mannans of *C. albicans* are responsible for adherence of yeast forms to spleen and lymph node tissue. Infect. Immun. 61:2578–2584).

One of the adhesin sites has been identified to structure (Li, R. K., et al. 1993. Chemical definition of an epitope/adhesin molecule on *C. albicans*. J. Biol. Chem. 268:18293–18299), and the nature of the macrophage ligand is under investigation (Han, Y., et al. 1994. Mouse sialoadhesin is not responsible for *C. albicans* yeast cell binding to splenic marginal zone macrophages. Infect. Immun. (62: 2115–2118).

The present inventors set out to determine whether antibodies are protective against disseminated candidiasis. Given the complexity of adhesins and variable character of the cell surface of *C. albicans*, the role of antibodies in host defense against disseminated candidiasis has remained a contentious issue. Evidence that argues against a protective role for antibodies is derived mostly from clinical observations showing that principitin antibodies specific for candidal antigens can be detected in the sera of most patients with disseminated or deep-seated candidiasis. Experimentally, while some investigators reported that human antibodies specific for *C. albicans* enhance phagocytic cell uptake of fungal elements (Diamond, R. D., et al. 1978. Damage to pseudohyphal forms of *C. albicans* by neutrophils in the absence of serum in vitro. J. Clin. Invest. 61:349–359), others concluded that specific antibodies may block phagocytosis of *C. albicans* (LaForce, F. M., et al. 1975. Inhibition of leukocyte candidacidal activity by serum for patients with disseminated candidiasis. J. Lab. Clin. Med. 86:657–666; and Walker, S. M. et al. 1980. A serum-dependent defect of neutrophil function in chronic mucocutaneous candidiasis., J. Clin. Pathol. 33:370–372).

The suggestion by some that IgE responses may inhibit phagocytosis by human neutrophils of *C. albicans* indicates the importance of investigating the protective nature of Ig subtypes (Berger, M., et al. 1980. IgE antibodies to *Staphylococcus aureus* and *C. albicans* in patients with the syndrome of hyperimmuno-globulin E and recurrent infections. J. Immunol. 125:2437–2443). In addition, none of the early investigators addressed the issue of antibody specificity. In one study on susceptibility of various kinds of immunodeficient mice to hematogenous disseminated candidiasis, the importance of candidal-specific antibodies was dismissed and, instead, T-cell-mediated immunity was concluded as the important acquired-specific host defense (Cantorna, M. T., et al. 1991. Acquired Immunity to Systemic Candidiasis in Immunodeficient Mice. J. Infect. Dis. 164:936–943). The conclusions were, however, contended by others (Matthews, R. et al. 1992. Acquired immunity to systemic candidiasis in immunodeficient mice: Role of antibody to heat-shock protein 90. J. Infect. Dis. 166:1193–1194) because an alternative interpretation is that specific antibodies were not induced in the immunodeficient animals.

However, antibodies appear to assist the host in resisting disseminated candidiasis. Mourad and Friedman showed that mice with high antibody titers against *C. albicans* were relatively resistant against hematogenously disseminated disease, and immunity was transferrable to naive mice via the anti-serum (Mourad, S., et al. 1961. Active immunization of mice against *C. albicans*. Proc. Soc. Exp. Biol. Med. 106:570–572; and Mourad, S., et al. 1968. Passive immunization of mice against *C. albicans*. Sabouraudia 6:103–105).

These findings were corroborated by Pearsall who reported that serum could transfer protection to naive animals against a deep seated infection with *C. albicans* (Pearsall, N. N., et al. 1978. Immunologic responses to *C. albicans*. III Effects of passive transfer of lymphoid cells or serum on murine candidiasis. J. Immunol. 120:1176–1180). Sensitized lymphoid cells transferred cutaneous delayed hypersensitivity to naive mice, but did not protect these animals against the deep seated disease.

In 1978, Domer's group determined that *C. albicans* cutaneous infection provoked mice to produce antibodies specific for the fungus, and such animals were less susceptible to disseminated candidiasis than control (Giger, D. K., et al. 1978 Experimental murine candidiasis: pathological and immune responses to cutaneous inoculation with *C. albicans*. Infect. Immun. 19:499–509). Further experiments supported a specific protective effect. If B-cells were depleted by anti-μ therapy, the mice were unable to make antibody in response to the cutaneous infection, their T-cell activities appeared unaffected, but these animals were more susceptible to disseminated disease than controls (Kuruganti, U., et al. 1988. Nonspecific and Candida-specific immune responses in mice suppressed by chronic administration of anti-μ. J. Leukocyte Biol. 44:422–433). These experiments were confirmed by other investigators (Maiti, P. K., et al. 1985. Role of antibodies and effect of BCG vaccination in experimental candidiasis in mice. Mycopathologia 91:79–85).

In unrelated observations, production of antibodies against conserved epitopes of candidal and human heat-shock protein (hsp) 90 correlated with the ability of experimental animals to resist disseminated candidiasis. Patients who recovered from disseminated disease produced this antibody (Matthews, R. et al. 1992. Acquired immunity to systemic candidiasis in immunodeficient mice: Role of antibody to heat-shock protein 90. J. Infect. Dis. 166:1193–1194) and anti-hsp 90 from patient sera transferred to mice protection against disseminated candidiasis (Matthews R. C., et al. 1991. Autoantibody to heat-shock protein 90 can mediate protection against systemic candidosis. Immunol. 74:20–24). Although the authors claimed that the patient's sera contained antibodies only against hsp 90, the detection method used (i.e., PAGE and Western blotting) was unlikely to show antibodies against the candidal cell surface PMP.

The surface of *C. albicans* is variable, and the inventors have obtained evidence that immunodominant antigens may not necessarily be involved in critical host-*C. albicans* interactions, such as adherence events. For example, a major antigen expressed on the surface of serotype A strains is not an adhesin. Since *C. albicans* readily activates the alternative complement cascade, and C3 deposition on the candidal cell surface promotes ingestion by phagocytic cells an opsonic role for specific antibodies may not be very important (Morrison, R. P., et al. 1981. In vitro studies of the interaction of murine phagocytic cells with *C. albicans*. J. Reticuloendothel. Soc. 29:23–34).

The present inventors show that vaccine protected mice by production of antibodies specific for candidal adhesins. Perhaps the ideal protective antibody response would prevent adherence of circulating yeast cells to endothelial and subendothelial surfaces, while enhancing or not affecting an interation with phagocytic cells.

Whereas the bulk of clinical studies indicate an importance of T-cell dependent cell mediated immunity (CMI) in host resistance to mucosal candidiasis, neither clinical observations nor most animal experimental studies show that CMI plays a major role in resistance to disseminated candidiasis. (See Brawner, D. L., et al. 1992. Oral candidiasis in HIV-infected patients. AIDS Reader July/August:117–124; Fidel, P. L., et al. 1993. Candida-specific cell-mediated immunity is demonstrable in mice with experimental vaginal candidiasis. Infect. Immun. 61:1990–199520; Odds, F. C. 1988. Candida and candidiasis. Bailiere Tindall, London.)

T-cell dependent cell mediated immune (CMI) responses appear not to be involved in host resistance to disseminated candidiasis. A possible explanation is that CMI is overshadowed in importance by the action of neutrophils, macrophages, specific antibodies and other factors.

The inventors have studied disseminated candidiasis, and immune responses to *C. albicans*, in normal and immunocompromised mice for over twenty years. Recently the variable nature of the cell surface of *C. albicans* and antibody responses by mice to *C. albicans* cell wall antigens have been analyzed.

The function of the moieties on the fungal cell surface and adherence properties was investigated. Work progressed from characterizing the surface of *C. albicans* to an understanding of functions of cell surface moieties as they relate to candidal-host interactions.

Events that occur within 30–45 min after yeast cells of *C. albicans* gain access to the circulation of the host and become attached to deep tissue sites where the fungal cells may adhere either to a host phagocytic cell or to a non-phagocytic cell site, such as an endothelial cell were studied.

Clinical isolates of *C. albicans* are either serotype A or B, but one or the other serotype may predominate in human subjects depending on the immunological status of the patient. The prototype strains used are CA-1 (serotype A) and A-9 (serotype B) that have been extensively studied in the laboratory.

An important consideration in all work on *C. albicans* is the inherent variability potential of the species. Culture conditions and handling of the strains have been standardized to stabilize their characteristics and allow for long-term reproducible results.

EXAMPLE 1

Culturing of *C. albicans* to maintain constant characteristics. Strains of *C. albicans* show genetic instabilities and antigenic variability. To maintain constancy in surface characteristics throughout the experiments, the strains will be stored in 50% glycerol at −20° C., and as cell pellets in sterile water at −20° C. Fresh new working cultures will be prepared form the frozen stocks every week. For preparation of hydrophilic cells, a loopful of the glycerol stock will be used to inoculate 25 ml of GYEPB (2% glucose, 0.3% yeast extract, 1% peptone broth) in a 50 ml Erlenmeyer flask, the culture will be incubated for 24 h at 37° C. under aeration by rotation at 160–180 rmp, then serially transferred to fresh GYEPB (e.g., 3 drops of culture may be transferred to 25 ml GYEPB three to six times at 24 h intervals and incubated as above). This procedure produces almost 100% hydrophilic yeast forms in stationary phase of growth. Yeasts are harvested by centrifugation, the pelleted cells are washed three times in ice-cold deionized water, held on ice as pelleted cells until use (up to 2 h), and suspended to the appropriate working concentration in the appropriate medium.

Alternatively, yeast cells may be grown to have a hydrophobic cell surface (Hazen, K. C., et al. 1991. Differential adherence between hydrophobic and hydrophilic yeast cells of *C. albicans*. Infect. Immun. 59:907–91212; Hazen, K. C., et al. 1986. Influence of growth conditions on cell surface hydrophobicity of *C. albicans* and *Candida glabrata*. Infect. Immun. 54:269–271). The cultures are grown exactly as above, except that incubations are at 24° C.

A microsphere assay is used to monitor the percentage of cells that have a hydrophobic or hydrophilic cell surface (Hazen, K. C., et al. 1987. A polystyrene microsphere assay for detecting surface hydrophobicity variations within *C. albicans* populations. J. Microbiol. Methods. 6:289–299). Equal volumes (100 µl) of yeast cells ($2 \times 10^6$/ml) and hydrophobic (i.e., low sulfate) blue polystyrene microspheres (diameter, 0.801 µm; ca. $9 \times 10^5$ microspheres per ml (Serva Fine Biochemicals, Wesburg, N.Y.), each suspended in sodium phosphate buffer (0.05M, pH 7.2), will be placed into acid-washed glass tubes ($12 \times 75$ mm), equilibrated to 23° C. for 2 min and vigorously mixed for 30 sec. Yeast cells with three or more attached microspheres are considered to by hydrophobic.

The protocol for β-mercaptoethanol extraction of the adhesins as part of the cell wall phosphomannoprotein complex (2ME extract) is the same as previously defined in our laboratory and further detailed below (Kanbe, T., et al. 1993. Evidence that mannans of *C. albicans* are responsible for adherence of yeast forms to spleen and lymph node tissue. Infect. Immun. 61:2578–2584).

EXAMPLE 2

Tissue adherence characteristics of *C. albicans* and adhesin isolation. By use of an ex vivo adherence assay, the adherence characteristics of hydrophilic and hydrophobic yeast cells to mouse splenic and lymph node tissue was examined (Cutler, J. E., et al., 1990, Characteristics of *Candida albicans* adherence to mouse tissues. Infec. Immun. 58:1902–1908); Han, Y., et al. 1993. Binding of *C. albicans* yeast cells to mouse popliteal lymph node tissue is mediated by macrophages. Infect. Immun. 61:3244–3249; and Hazen, K. C., et al. 1991. Differential adherence between hydrophobic and hydrophilic yeast cells of *C. albicans*. Infect. Immun. 59:907–91212).

It was found that *C. albicans* hydrophilic yeast cells specifically adhere to mouse splenic marginal zone macrophages (Cutler, J. E., et al. 1990. Characteristics of *C. albicans* adherence to mouse tissue. Infect. Immun. 58:1902–1908; Kanbe, T., et al. 1992. Evidence that *C. albicans* binds via a unique adhesion system on phagocytic cells in the marginal zone of the mouse spleen. Infect. Immun. 60:1972–1978). An essentially identical binding pattern of yeast cells to the mouse spleen occurs in vivo following an intravenous (i.v.) presentation of fungal cells (Tripp, D. L. et al. 1994. Evidence for complement independent in vivo adherence of *C. albicans*. Abstr. Annu. Meet. ASM.).

Complement may play a role in organ distribution of *C. albicans* from the blood. The pattern of yeast cell adherence to the spleen is not influenced by the presence of fetal bovine serum, or the absence of serum in the ex vivo assay (Cutler, J. E., et al. 1990. Characteristics of *C. albicans* adherence to mouse tissue. Infect. Immun. 58:1902–1908; and Riesselman, M. H. et al. 1991. Improvements and important considerations of an ex vivo assay to study interactions of *C. albicans* with splenic tissue., J. Immunol. Methods 1450:153–160). However, if yeast cells are opsonized in fresh mouse serum without detectable antibodies against *C. albicans* (Morrison, R. P., et al. 1981. In vitro studies of the interaction of murine phagocytic cells with *C. albicans*. J.

Reticulo-endothel. Soc. 29:23–34) binding to the marginal zone is enhanced by 50–200% (Tripp, D. L. et al. 1994. Evidence for complement independent in vivo adherence of *C. albicans*. Abstr. Annu. Meet. ASM.).

In vivo binding of yeast cells to the splenic marginal zone appears unaffected by complement opsonization. Yeast cells become opsonized by incubation for 30 min at 37° C. in the presence of 2.5% (or more) fresh mouse serum (Morrison, R. P., et al. 1981. In vitro studies of the interaction of murine phagocytic cells with *C. albicans*. J. Reticuloendothel. Soc. 29:23–34). The opsonization is due to activation of the alternative complement cascade and is required for optimal phagocytosis by mouse peritoneal macrophages. When $8 \times 10^8$ yeast cells are complement opsonized and given i.v. to mice, the number of yeast cells that bind to the splenic marginal zone is essentially the same as compared to binding of non-opsonized yeast cells. Furthermore, mice made complement C3 deficient by treatment with cobra venom factor still show the same yeast cell adherence in vivo as in complement sufficient animals (Tripp, D. L. et al. 1994. Evidence for complement independent in vivo adherence of *C. albicans*. Abstr. Annu. Meet. ASM).

These results have been confirmed by Kozel's group who used a different approach. Cobra venom depleted C3 mice and normal control animals were given viable yeast cells. Forty-five min. later the animals were sacrificed and the number of fungal colony forming units (cfu) in the spleen of C3 depleted mice was similar to splenic cfu of normal controls. A very interesting finding, however, was that C3 depleted mice had higher counts in the lungs as compared to normal controls, implying that complement may play a role in the organ distribution of *C. albicans* yeast cells from the circulation.

Adhesins responsible for attachment of hydrophilic yeasts to splenic marginal zone are glycans (mannans) and not protein. The adhesins responsible for attachment of hydrophilic yeast cells to the marginal zone macrophages are solubilized from the fungal cell surface by extraction with β-mercaptoethanol (2ME extract) (Kanbe, T., et al. 1993. Evidence that mannans of *C. albicans* are responsible for adherence of yeast forms to spleen and lymph node tissue. Infect. Immun. 61:2578–2584).

EXAMPLE 3

Preparation of Antigen (2ME extract or phosphomannoprotein, which contains the adhesins)

2-ME extract of *C. albicans* strain CA-1 was isolated and used for immunization by inserting the 2ME extract within liposomes.

1. Medium: GYEP broth Glucose 2% Yeast extract 0.3% Peptone 1%/per liter
2. *C. albicans* strain Strain CA-1 culture by 4 to 6 times transferring into a fresh medium (GYEP) was used as a starter culture. 5 ml of the culture was inoculated into 1.2 liter GYEP broth medium, incubated at 37° C. under constant aeration by rotation of flasks at 180 rpm, incubated 22–28 h.

3. Extract (how to prepare the 2-ME extract.)
2-ME Extraction of the surface of *C. albicans*
[Recommended tubes, rotors, etc. will vary with batch size.]

1. Count a 1:100 dilution of the GYEP yeast culture. Estimate the total number of cells and wet weight in the culture $10^{10}$ cells/g wet weight). Alternatively weigh the centrifuge tube before and after collecting the pellet to determine yeast wet weight. [Grams wet weight is used in steps 8 and 9 below to determine the required volumes of 0.1M EDTA pH 9.0 and mercaptoethanol.]

2. Pellet Candida for 10 min. by centrifugation at 2,500× g, 4°–6° C.

3. Wash the pelleted cells 2× with cold deionized water ($dH_2O$).

4. Suspend the washed cells in 250 ml of $dH_2O$.

5. Pellet the cells by centrifugation at 5,000×g for 10 min. and discard the supernatant liquid.

6. Suspend the cells in 250 ml of cold 0.1M ethylenediamine tetraacetic acid (EDTA), pH 7.5.

7. Pellet the cells at 5,000×g for 5 min and discard supernatant material.

8. Suspend to 2.0 ml/g. wet weight in 0.1M EDTA pH 9.0, at room temperature.

9. In a fume hood, add 2-mercaptoethanol to 0.3M to the cell suspensions, cap tightly and invert to mix.

10. At room temperature, mix (by inverting the tube) every 5 min. for 30 min.

11. Pellet the cells at 5,000×g for 10 min.

12. Collect the supernatant material and centrifuge the supernatant at 5,000×g until the supernatant material (2-ME extract) is clear.

13. Dialyze the 2-ME extract against cold $dH_2O$, change the wash every 2–6 hours until the odor of 2-mercaptoethanol is no longer apparent.

14. Concentrate by lyophilization. The dried product is referred to as the 2-ME extract. The 2-ME extract contains the phosphomannoprotein complex. Candida adhesins are contained within the mannan portion of the complex.

At concentrations less than 1 μg/ml, the 2ME extract blocks binding of hydrophilic yeast cells to the splenic marginal zone macrophages. In addition, latex beads coated with the 2ME extract bind to the splenic macrophages in a pattern identical to that of whole yeast cells. The activity of the adhesins in the 2ME extract is not affected by boiling or proteolytic enzymes, but is destroyed by periodate oxidation and α-mannosidase digestion.

These data strongly indicate that the adhesins are glycans, probably mannan, and not proteins. In addition, the 2ME extract can be fractionated further by proteinase K digestion and con A-affinity chromatography to yield an adhesin fraction, termed Fr.II that is practically devoid of detectable protein, yet retains full adhesin activity (Kanbe, T., et al. 1993. Evidence that mannans of *C. albicans* are responsible for adherence of yeast forms to spleen and lymph node tissue. Infect. Immun. 61:2578–2584).

The mannan nature of the adhesins is further supported by subsequent purification work which showed the adhesin activities to be associated with the mannan portions of the phosphomannoprotein (PMP) (FIG. 1). The PMP was degraded by mild acid hydrolysis, and the released oligomannosyl side chains were size separated by P-2 column chromatography (Li, R. K., et al. 1993. Chemical definition of an epitope/adhesin molecule on *C. albicans*. J. Biol. Chem. 268:18293–18299).

By use of mAb 10G (available from the lab of Dr. Cutler), a tetramannosyl chain was identified as the epitope to which mAb 10G is specific. The tetramannosyl is a β-1,2-linked straight-chained tetramannose and is one of the adhesin sites in the PMP. The purified tetramannose blocks binding of yeast cells to the splenic marginal zone, and latex beads coated with the epitope bind to the marginal zone in a pattern essentially identical to yeast cell binding. This work represents the first identification to structure of an adhesin on the surface of *C. albicans*.

Further analysis of the acid-stable portion of the PMP (FIG. 1) revealed that adhesin activity is also associated with this part of the complex (Kanbe, T., et al. 1994. Evidence for adhesin activity in the acid-stable moiety of the phosphomannoprotein cell wall complex of *C. albicans*. Infect. Immun. 62:1662–1668).

The inventors induced in mice an antibody response against 2-ME extract and have obtained nine mAbs specific for this fraction. FIG. 1 is a simplified model of cell wall phosphomannoprotein (PMP) of *C. albicans* serotype B based on a structure by others (Kobayashi, H., et al. 1990. Structural study of cell wall phosphomannan of *C. albicans* NIH B-792 (serotype B) strain, with special reference to $^1$H and $^{13}$C NMR analyses of acid-labile oligomannosyl residues. Arch. Biochem. Biophys. 278:195–204). The number of mannose units in each oligomannosyl side chain ranges from 1–7. The backbone phosphomannan portion may be tandemly repeated. Asp, asparagine.

The 2ME extract was then formulated into liposomes to test its effectiveness as a vaccine. The method of preparing the liposomes is set forth below.

EXAMPLE 4

Preparation of multilamellar liposomes contained 2-ME extract (L-2ME) or PBS (L-PBS).
Materials:
 1. Cell wall antigens (2-ME extract)
 2. L-α-phosphatidylcholine (L-α-lechithin): Type XI-E, from frozen egg yolk, P-2772 (Lot#-112H8362), chloroform solution (100 mg/ml), Sigma, St. Louis, Mo.
 3. cholesterol: 99% grade, FW=386.7, C-8667 (Lot#-110H8473), chloroform solution (100 mg/ml), Sigma.
 4. chloroform: 9180-01, J. T. Baker, Phillipsburg, N.J.
 5. methanol: A452-4, Fisher Chem.
 6. PBS: Dulbecco's phosphate buffered saline, pH=7.4, Sigma.
Procedures:
 1. Put 200 μl of phosphatidylcholine and 30 μl of cholesterol in chloroform solutions into 10 ml methanol/chloroform (1:1) contained in a 500 ml round bottom flask.
 2. Evaporate at 37° C. (indicator=set at 2) at low vacuum rotation until a thin layer film forms on the interior of the flask.
 3. Dissolve the dried lipid film in 10 ml chloroform and remove the chloroform by low vacuum rotary evaporation at 37° C.
 4. Add 5 ml of PBS containing 10 mg of the solubilized cell wall antigen (2-ME extract) to the flask.
 5. Disperse the lipid film layer into the 2-ME extract solution by gentle rotation at room temperature for 10 min. For empty control liposome (L-PBS), disperse the thin film in 10 ml PBS only.
 6. Hold the suspension at room temperature for 2 hrs. and then sonicate at 20° C. in a water bath sonicator (FS5, Fisher Scientific) for 3 min.
 7. Maintain the suspension at room temperature for another 2 hrs. to allow swelling of the liposomes.
 8. Centrifuge at 1,000×g (3,000 rpm with SS34, Sorvall RC-5B Refrigerated Superspeed Centrifuge, DuPont) for 30 min at 16° C. to remove non-liposome associated antigen from liposome encapsulated 2ME-extract.
 9. Suspend the liposome in 10 ml PBS and centrifuge again. Repeat these procedures two more times.
 10. The liposome-encapsulated 2-ME extract is finally suspended in 4 ml PBS and stored at 4° C. under nitrogen.
 11. Determine the amount of 2-ME extract entrapped in liposomes. The liposome-2-ME extract complex should show a yellowish color by the phenol-sulfuric acid test for carbohydrates, thus indicating the presence of 2-ME extract in the liposomes. The phenol-sulfuric acid procedure (Dubois) is done as follows: place 60 μl of the liposome-2ME extract preparation into a well of a microtiter plate and mix with 30 μl of 5% phenol solution. Incubate the mixture at 21°–23° C. for 2 min and add 120 μl of concentrated sulfuric acid. Observe a color change from colorless to yellow for the positive reaction. Read the color change at an optical density of 490 nm. By use of this optical density (OD) was compared to the standard dilutions of 2-ME-extract in PBS. The results were as follows:

| Amt. of 2-ME per 5 ml PBS | O.D. at 490 nm |
|---|---|
| 1. 10 mg/5 ml | 0.318 |
| 2. 5 mg/5 ml | 0.159 |
| 3. 2.5 mg/5 ml | 0.078 |

As determined by the Dubois (phenol-sulfuric acid) test for carbohydrates the amount of 2-ME extract entrapped in liposomes was 178 μg per 0.2 ml of the preparation. Varying amounts of adhesin fractions may be added during formation of the liposomes to determine the effect on final adhesin concentration that becomes complexed.

EXAMPLE 5

Liposomes made of phosphatidycholine/cholesterol which contained 178 μg of 2ME extract per 0.2 ml preparation were used as the vaccine preparation. Mice were immunized by giving 5 weekly intravenous (i.v.) injections of varying doses (0.1–0.3 ml) of the liposome-2ME extract per animal. One group of mice received 0.2 ml of the preparation on days 1, 3, 5 and 10, and then weekly for two more weeks. Control mice received either liposomes prepared with the 2ME extract diluent (phosphate-buffered saline, PBS), PBS alone, or an equivalent amount of 2ME extract in PBS. Each week, the animals were bled and tested for agglutinins by determining if the sera agglutinated whole yeast cells or latex beads coated with the 2ME extract. Mice immunized weekly for 5 weeks with 0.1 ml or 0.2 ml of the preparation gave the highest agglutinin titers (agglutinin titers were consistently about 40). Mice immunized against 2ME extract in PBS produced titers less than 5, or none at all.

Thus the liposome-encapsulation method of antigen presentation induces in mice polyclonal antisera against antigens within the 2ME extract including candidal adhesins, and will allow for subsequent isolation of mAbs against these antigens.

Liposome-encapsulated 2ME extract promotes strong antibody responses, but the 2ME extract alone is not very immunogenic in mice. Adjuvants, such as those of Ribi (Ribi Adjuvant System) and Hunter (TiterMax) are not very effective in inducing mice to make antibody against the glycan moieties with the 2ME extract. Less than 50% of the mice sensitized against the 2ME extract-Ribi adjuvant combination produced a slight antibody response, and none of the animals responded when the Hunter adjuvant was used.

A very significant advance was made upon the finding that liposome-encapsulated 2ME extract promotes a strong antibody response in 100% of the immunized mice. The mechanism by which liposomes cause a heightened antibody response is unknown, but in work unrelated to ours, others have also obtained excellent results with this approach (Livingston, P. O., et al. 1993. GD3/proteosome vaccines induce consistent IgM antibodies against the ganglioside GD3. Vaccine II:1199–2004; Wetzler, L. M. et al. 1992. Gonococcal sporin vaccine evaluation: comparison for proteosomes, liposomes, and blobs isolated from rmp deletion mutants., J. Infect. Dis. 166:551–555).

EXAMPLE 6

Production of mAbs against cell surface antigens of *C. albicans*. One of the mAbs (mAb 10G) is specific for an adhesin site in the acid-labile portion of the PMP contained in the 2-ME extract and the inventors have obtained nine new mAbs against the 2-ME extract. Fusion, cloning and selection methods have been used extensively and described in detail (Brawner, D. L., et al. 1984. Variability in expression of a cell surface determinant on *C. albicans* as evidenced by an agglutinating monoclonal antibody. Infect. Immun. 43:966–972; Cutler, J. E., et al. 1994. Production of monoclonal antibodies against mannan determinants of *C. albicans*, B. Maresca and G. S. Kobayashi (ed.), In: Molecular Biology of pathogenic fungi; A Laboratory Manual. Telos Press, p.197–206; and Li, R. K., et al. 1991. A cell surface/plasma membrane antigen of *C. albicans*. J. Gen. Microbiol. 137:455–464).

Cell-mediated immunity may not be important in resistance to disseminated candidiasis. Some investigators have reported that macrophages are important, while others have found no evidence that macrophages protect (Qian, Q. et al. 1994. Elimination of mouse splenic macrophages correlates with increased susceptibility to experimental disseminated candidiasis. J. Immunol. 152:5000–5008). Perhaps the biggest pitfall in many of these works is that the approaches used to eliminate macrophages were non-specific.

In the present studies (Qian, Q. et al. 1994. Elimination of mouse splenic macrophages correlates with increased susceptibility to experimental disseminated candidiasis. J. Immunol. 152:5000–5008), mouse splenic macrophages were eliminated by intravenous (i.v.) delivery of liposome-entrapped dichloromethylene diphosphonate (L-$Cl_2$MDP). This liposome conjugate becomes selectively taken up by macrophages, which causes their elimination.

Splenic tissue sections immunoperoxidase stained with mAbs against marginal zone macrophages (mAB MONTS-4), red pulp macrophages (mAB SK39) and neutrophils (mAB SK208) showed that 36 h after L-$Cl_2$MDP treatment, macrophages but not neutrophils were depleted, and circulating neutrophils responded normally to an irritated peritoneum and showed normal phagocytic ability. That is, in response to thioglycollate in the peritoneum, neutrophils migrated in normal numbers to the peritoneal cavity and expressed the normal activation phenotype of high mac-1 (integrin) and low Mel-14 (L-selectin) antigen levels. These neutrophils also showed normal ability to ingest *C. albicans* yeast cells in vitro and in vivo. However, the spleens from L-$Cl_2$MDP-treated mice lost their ability to bind yeasts, which agrees with our previous findings that hydrophilic yeast cells bind specifically to marginal zone macrophages.

When macrophage depleted mice were systemically challenged with *C. albicans*, clearance of viable fungal elements from blood was slower, their kidneys had higher recoverable cfu, and neither BALB/c nor nu/nu mice survived as long as control mice. Mice given L-$Cl_2$MDP recovered most of their macrophage function by 56 days and became normal in their resistance to *C. albicans*.

These results indicate that macrophages play an important role in host resistance to disseminated candidiasis. The similar results obtained with normal mice and the congenitally thymic deficient (nude) mouse indicate that the mechanism of protection by microphages does not involve activation of T-cell functions. This result is important, because it is consistent with earlier reports indicating that cell-mediated immunity may not be critical in resistance of mice to deep-seated or disseminated candidiasis (Mourad, S., et al. 1968. Passive immunization of mice against *C. albicans*. Sabouraudia 6:103–105 ; Pearsall, N. N., et al. 1978. Immunologic responses to *C. albicans*. III Effects of passive transfer of lymphoid cells or serum on murine candidiasis. J. Immunol. 120:1176–1180). These results did not, however, negate the hypothesis that antibodies play a role in host defense against disseminated candidiasis.

EXAMPLE 7

2ME extract from a *Cryptococcus neoformans* acapsular mutant does not have adhesin activity and serves as a negative control. For negative control purposes a fungal 2ME extract that does not contain candidal-like adhesin activity was obtained. Extensive investigations were done on various strains of *Saccharomyces cerevisiae* and on the Ballou mutant strains mnn1, mnn2 and mnn4 (Raschke, W. C. et al. 1973. Genetic control of yeast mannan structure, Isolation and characterization of yeast mannan mutants, J. Biol. Chem. 248:4660–4666). The strains were grown at various temperatures and yeast from different phases of growth were analyzed for their binding characteristics to mouse splenic tissue. These experiments are summarized by stating that *S. cerevisiae* produces some, but not all, of the candidal adhesins responsible for yeast cell binding to the splenic marginal zone. To obtain a fungal 2ME extract that did not have the ability to block adherence of *C. albicans* to splenic tissue, the acapsular mutant strain 602 of *C. neoformans* was examined (Kozel, T. R., et al. 1971. Nonencapsulated variant of *Cryptococcus neoformans* 1. Virulence studies and characterization of soluble polysaccharide. Infect. Immun. 3:287–294).

*C. neoformans* strain 602 log and stationary phase cells were removed form the various growth conditions and tested for adherence to splenic tissue in the ex vivo assay. None of these growth conditions yielded adherent yeast cells. Stationary phase cells extracted by the β-mercaptoethanol method gave a water soluble cell wall material that did not affect binding of *C. albicans* yeast cells. That is, in the ex vivo assay, pretreatment of splenic sections with 10 μg, 25 μg and 100 μg of the cryptococcal 2ME extract had no detectable effect on binding of *C. albicans* hydrophilic yeast cells to the marginal zone, as compared to over 95% inhibition of binding due to pretreatment of splenic tissues with 1 μg of 2ME extract from *C. albicans* yeast cells.

The chemical nature of the cryptococcal 2ME extract is apparently mostly glucan (James, P. G., et al. 1990. Cell-wall glucans of *Cryptococcus neoformans* CAP 67. Carbohyd. Res. 198:23–38) which serves as a non-specific control material.

EXAMPLE 8

To test whether *C. albicans* serotype differences are important, the inventors prepared adhesin fractions from serotype A and B strains (CA-1 and A-9, respectively). Both adhesin fractions cause identical dose response inhibition of binding of either serotype A or B strain yeast cells. Data show animals vaccinated against serotype A 2ME extract became protected against disseminated candidiasis by the serotype B strain. Because serotype B strains apparently contain all antigens found on serotype A strains, but serotype A strains have one (or more) cell surface antigens not found on serotype B strains (Hasenclever, H. F., et al. 1961. Antigenic studies of Candida I. Observation of two antigenic groups in *C. albicans.* J. Bacteriol. 82:570–573; and Hasenclever, H. F., et al. 1961. Antigenic studies of Candida II. Antigenic relation of *C. albicans* group A and group B to *Candida stellatoidea* and *Candida tropicalis.* J. Bacteriol. 82:574–577). Most of the adhesin isolations are from the serotype A strain.

EXAMPLE 9

Mice represent the simplest and most accepted experimental mammalian model of human candidiasis. Work derived from the survival and cfu experiments is more directly applicable to human needs than other non-animal studies proposed.

Male and female BALB/c and BALB/c outbred crosses are used to test the ability of various non-toxic vaccine to induce antibody responses. These mouse strains and thymic deficient (nude) mice on a BALB/c background and SCID mice are used for testing the ability of antibodies to protect animals against disseminated candidiasis. In addition, colonies of BALB/c mice crossed with an outbred mouse to yield the vigorous strain (BALB/c ByJ x Cri:CD-1(1CR)BR)F1, and henceforth referred to as CD-1, are also available from Montana State University. Initially, groups of three animals are used to assess the efficacy of the immunizations in terms of antibody titers. The number of animals used is based upon numbers required for statistical analysis. The experiments are evaluated by either fungal colony forming units (cfu) in animal organs retrieved well before ill-effects of the disease are apparent, or by animal survival.

Assessment of the adhesin-liposome preparations in mice. The vaccine preparations are assessed by determining their relative ability to induce antibody responses in mice. In studies it was found that 0.1–0.2 ml of the liposome-2ME extract complex is more immunogenic than other doses, and weekly boosters work best. Work was performed primarily on female BALB/c mice which have relatively high innate resistance to disseminated candidiasis (Hector, R. F., et al. 1982. Immune responses to *C. albicans* in genetically distinct mice. Infect. Immun. 38:1020) and females are somewhat more resistant (Ashman, R. B., et al. 1991. Murine candidiasis; Sex differences in the severity of tissue lesions are not associated with levels of serum C3 and C5, Immunol. Cell Biol. 69:7–10; Domer, J. E. 1988. Intragastric colonization of infant mice with *C. albicans* induces systemic immunity upon challenge as adults. J. Infect. Dis. 157:950–958.).

Control groups: It was found that liposome-buffer (PBS) preparations neither induce antibody responses nor cause increased resistance in mice to disseminated disease, thus in work with BALB/c mice, these controls are omitted. As a control in all studies, mice are immunized against the adhesin fractions prepared in buffer (0.01M PBS) alone. Doses of adhesin for controls are determined by assessing the concentration of adhesins in the final liposome preparation. The results from these control animals, when compared with liposome-adhesin test mice, provide a better indication of the advantage offered by liposome encapsulation. A reliable determination of 2ME extract adhesin content can be made by the phenol-sulfuric acid method of Dubois for carbohydrate. For adhesins with a high protein content, such as the hydrophobins or adhesins responsible for adherence to endothelial cells, protein assays (such as the BCA, Pierce), are used.

EXAMPLE 10

Immunization of mice against liposome-encapsulated 2-ME extract protects the animals against disseminated candidiasis. BALB/c female mice were immunized against the 2ME extract containing the mannan adhesins by encasing the extract in liposomes as indicated above. Each mouse from groups of 4 mice each were immunized against the liposome-2ME extract conjugate by giving 0.2 ml i.v. once each week for five weeks. All mice produced an agglutinin antibody titer from 20–40 in 100% of the mice as measured by agglutination of 2ME extract-coated latex beads.

Figure 2:
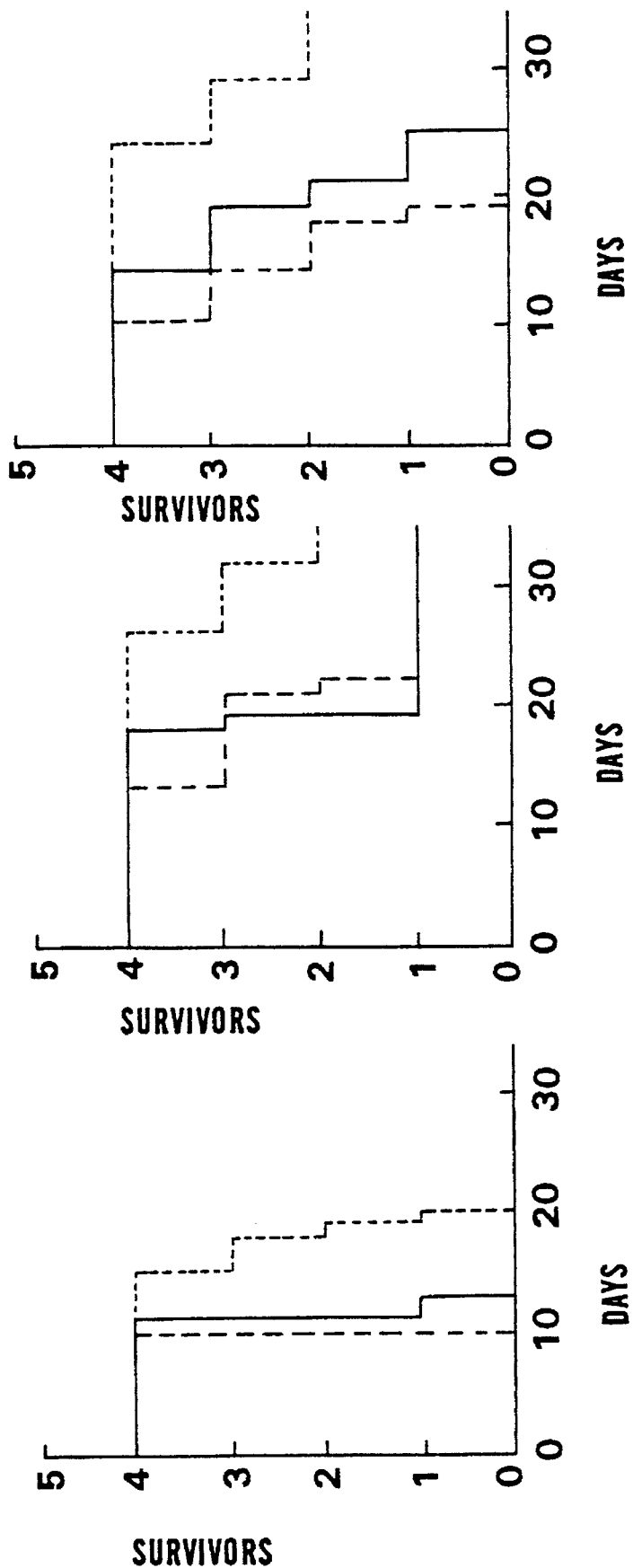
FIGS. 2A–2C show that mice immunized against the PMP (2ME extract) have increased survival times, as compared to buffer (PBS) controls, when challenged with a lethal dose of *C. albicans* yeast form cells. Animals that received the 2-ME extract-liposome complex (liposome-2ME extract) all developed high titers of serum antibodies specific for the extract.
Figure 3:
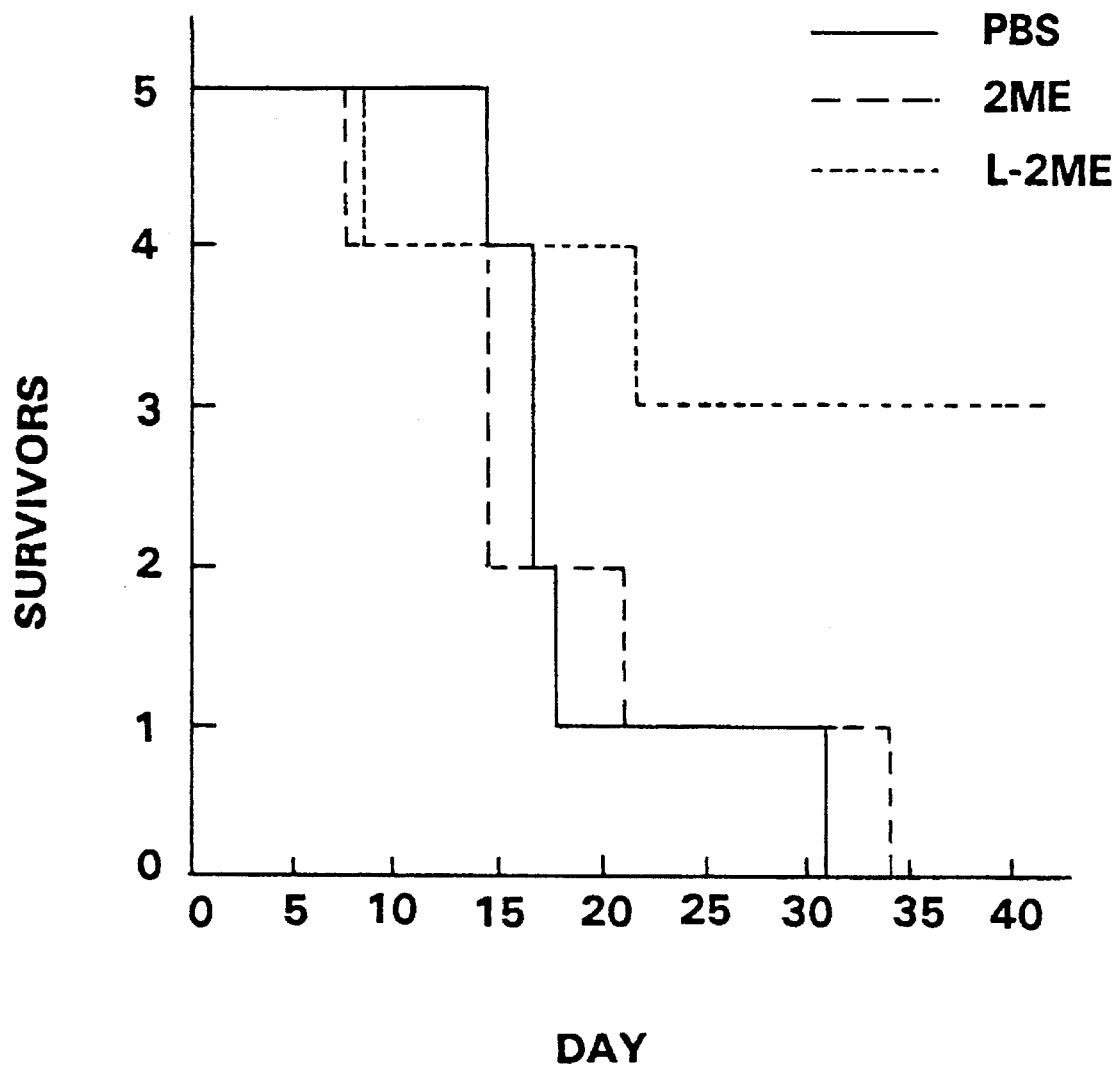
FIG. 3 shows in a different experiment that the protective effect of the liposome-2ME extract (L-2ME) is repeatable, and that the liposome part of the vaccine is necessary. In this experiment one group of mice received the 2ME extract in buffer (PBS) (the same amount of 2ME extract as complexed within the 2ME extract-liposome vaccine). These animals, which produced very little antibodies, did not show increased survival.
Figures 6A, 6B:
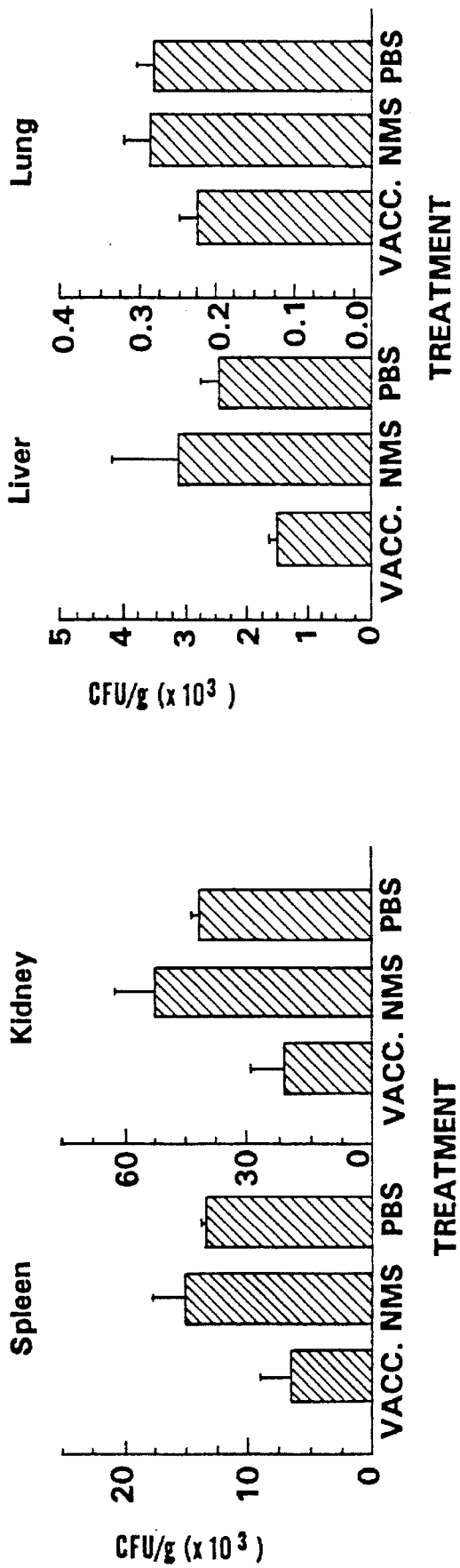
FIGS. 6A and 6B show that immune serum transfers protection against disseminated candidiasis. Disease severity was monitored by determining organ Candida burden (colony forming units, cfu) rather than survival.
Figure 7:
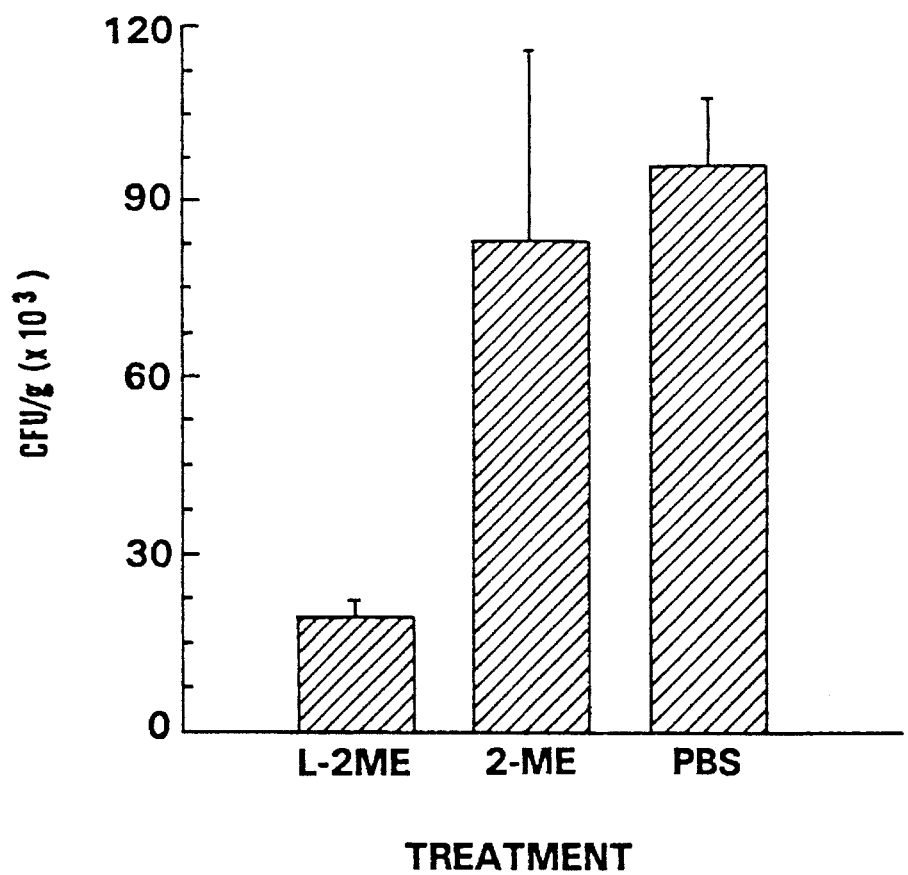
FIG. 7 shows a repeat of earlier experiments in which active immunization with the liposome-2ME extract vaccine protects animals against disseminated candidiasis. In this experiment disease severity was monitored by determining Candida burden (cfu) in kidney tissue. Because the kidney is a target organ in disseminated candidiasis, cfu determination is a reasonable alternative to survival curves.
Figure 8B:
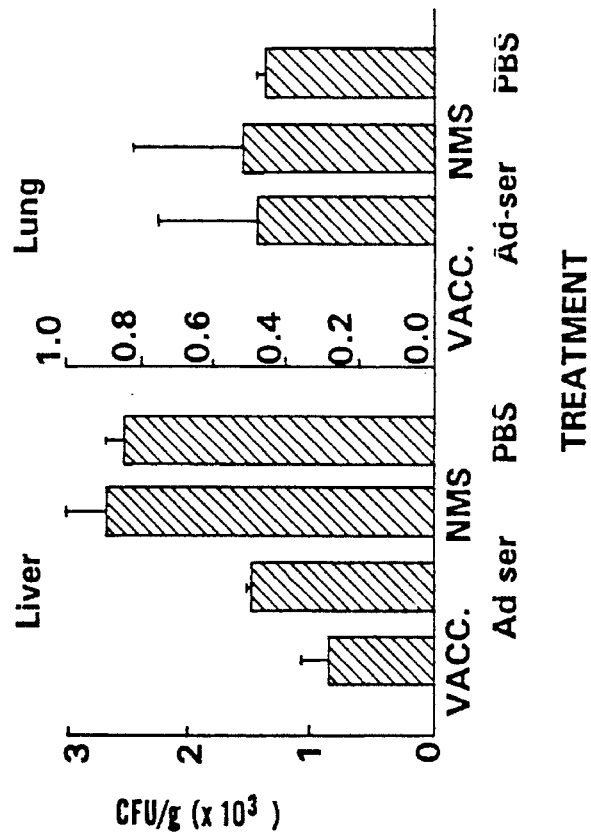
FIGS. 8A and 8B show that antibody may be responsible for the protective effect of the vaccine.
Figure 8A:
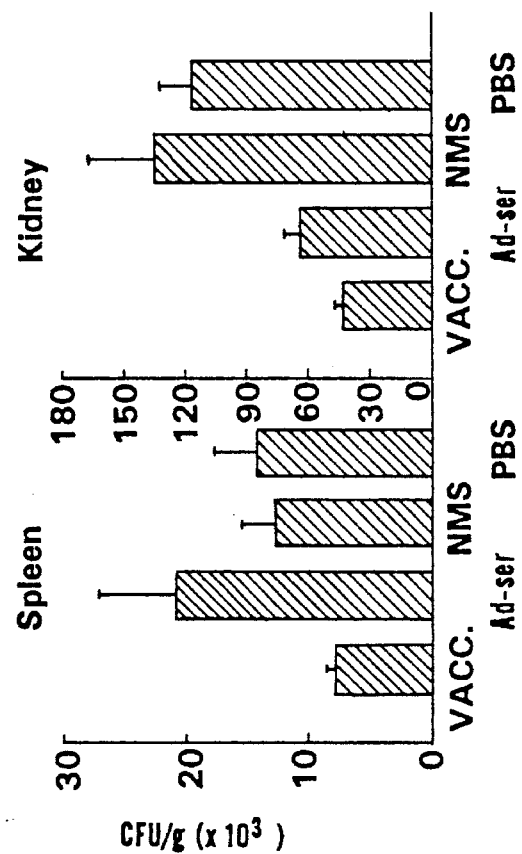

Mice immunized against the adhesin fraction showed increased survival times, as compared to PBS controls, when challenged with a lethal dose of *C. albicans* yeast form cells (FIG. 2). Although increased survival was more apparent when mice were challenged with $2.5 \times 10^5$ yeast cells (i.e., 0.2 ml i.v. of a concentration of yeast cells of $12.5 \times 10^5$/ml PBS), slight prolongation of survival was also noted in mice challenged with four times more yeast cells. In a repeat experiment, an additional group of mice was added that received 2ME extract in PBS (the same amount of 2ME extract as complexed within the 2ME extract-liposome vaccine). These animals, which did not produce antibodies, did not show increased survival (FIG. 3).

EXAMPLE 11

The inventors use passive transfer experiments to determine if antibodies are responsible for immunity. Immune sera from vaccinated animals, mAbs specific for the 2-ME extract of *C. albicans*, and mAbs against hydrophobic proteins of *C. albicans* are tested for their ability to protect naive animals against disseminated candidiasis. Immunologically competent mice, T-cell deficient (nu/nu), T- and B-cell deficient (SCID), and mice with induced neutropenia (by use of the anti-neutrophil antibody, mAb RB6-8C5) are tested. The ex vivo assay, the capillary tube shear-dependent adhesin assay, the endothelial adherence assay, and in vivo intravital microscopic methods are used to determine the effect of immune sera and protective mAbs on adherence characteristics of *C. albicans* to various host cells, tissues and glycoproteins. The effect of immune sera and mAbs on adherence characteristics of complement opsonized cells and unopsonized cells is examined. These results lead to preventative and therapeutic strategies for disseminated candidiasis.

To determine effectiveness of the vaccine, mice were immunized for the five week period to induce antibody responses against the adhesin fraction. They were then rendered immunocompromised by treatment with either mAb RB6-8C5, at 100 μg antibody/mouse i.v., that severely depletes neutrophils in vivo (Czuprynski, C. J., et al. 1994. Administration of anti-granulocyte mAb RB6-8C5 impairs the resistance of mice to Listeria monocytogenes infection. J. Immunol. 152:1836–1846; and Jensen, J. T., et al. 1993. Resistance of SCID mice to *C. albicans* administered intravenously or colonizing the gut rule of polymorphonuclear leukocytes and macrophages. J. Infect. Dis. 167:912–919), or cyclophosphamide given subcutaneously at 200 mg/kg mouse (Steinshamn, S. et al. 1992. Tumor necrosis factor and interleukin-6 in *C. albicans* infection in normal and granulocytopenic mice. Infect. Immun. 60:4003–4008).

The neutrophil suppressive effects of both treatments were confirmed by monitoring peripheral blood neutrophil counts, thioglycollate elicited peritoneal exudates, and assessing by FACScan analysis integrins and L-selectins (these techniques are defined in Qian, Q. et al. 1994. Elimination of mouse splenic macrophages correlates with increased susceptibility to experimental disseminated candidiasis. J. Immunol. 152:5000–5008).

At a low dose yeast challenge mice that were first vaccinated, then treated with mAB RB6-8C5 to make them neutropenic, and then challenged with *C. albicans* were still protected against disseminated candidiasis (as compared to the control mice that received treatment of mAB RB6-8C5 without prior vaccination (FIG. 9).

EXAMPLE 12

Immune serum neutralizes adhesins.

Sera from immune animals neutralize adhesin activity and blocks yeast attachment. Sera from vaccinated mice react with the adhesin fraction as evidenced by specific agglutination of adhesin-latex bead conjugates. When splenic sections are pretreated with 0.1 µg or more of the 2ME extract, *C. albicans* yeast cells will not bind to the tissues (Kanbe, T., et al. 1993. Evidence that mannans of *C. albicans* are responsible for adherence of yeast forms to spleen and lymph node tissue. Infect. Immun. 61:2578–2584, and our unpublished data).

However, 2ME extract will not inhibit yeast adherence if the extract is treated with antiserum from vaccinated animals. In this experiment, antiserum from BALB/c mice vaccinated against the 2ME extract was heat inactivated (56° C., 30 min) and produced a specific agglutinin titer of 40 against the 2ME extract-coated latex beads. In the test condition, 1 µg, 2 µg and 4 µg of 2ME extract was each mixed for 1 h on ice with a 1:4 dilution of antiserum. 100 µl of each was overlaid onto splenic cryosections for 15 min at 4° C., the mixtures were decanted, 100 µl of a suspension of yeast cells ($1.5 \times 10^7$/0.1 ml DMEM) was added to each tissue section for 15 min at 4° C., and yeast cell binding was quantified as previously described (Riesselman, M. H. et al. 1991. Improvements and important considerations of an ex vivo assay to study interactions of *C. albicans* with splenic tissue., J. Immunol. Methods 1450:153–160). Binding was compared with control sections pretreated with the 2ME extract concentrations but without antiserum, and with sections pretreated with normal mouse serum (NMS) (positive binding control). On control sections pretreated with 2ME extract at all three concentrations, binding of yeast cells to the marginal zone areas was less than 3% of positive binding control sections in which the pretreatment was NMS alone. An additional control, in which sections were pretreated with antiserum alone, showed that binding was not affected.

In the neutralization test, adherence of yeast cells to tissues pretreated with a combination of either 1 µg 2ME extract or 2 µg 2ME extract+anti-2ME extract antiserum was essentially the same as the positive binding control, and adherence was slightly reduced when tissues were pretreated with a combination of 4 µg 2ME extract+the antiserum.

When the mouse polyclonal anti-adhesin serum is mixed with yeast cells during their addition to the splenic tissues, yeast cell binding to the marginal zone macrophages is reduced. Addition of 25 or 50 µl of the anti-adhesin per 100 µl total of yeast cell suspension reduced by over 80% yeast cell binding in the ex vivo assay. Addition of 10 µl reduced binding by about 30%. NMS controls had no effect on binding.

The data from the above experiments indicate that the polyclonal antiserum produced in mice against the 2ME extract contains antibodies that neutralize candidal adhesins responsible for yeast cell binding to the marginal zone, the antibodies also block yeast cell attachment and the blocking ability of the antiserum appears to be dose dependent.

EXAMPLE 13

Evidence that immune serum transfers protection. In an experiment, immune serum (i.e., anti-2ME extract) was obtained from 20 vaccinated (the five week protocol) BALB/c mice. NMS was collected from mice that received an equal number of injections of PBS. Three groups of normal naive BALB/c mice (three/group) were given the following: Group 1 received 0.5 ml of immune serum i.p. on Day 1; Group 2 mice received 0.5 ml NMS from PBS-treated animals; Group 3 mice did not receive serum. Four hours later, each mouse was challenged i.v. with $5 \times 10^5$ yeast cells. The following day, the appropriate mice received either 0.2 ml antiserum, NMS or PBS. At the yeast cell challenge dose, it was expected that normal mice would begin to die of disseminated candidiasis by day 9 or 10 and all mice should die by day 20. In this experiment, however, the animals were sacrificed 48 h after challenge and the spleen, kidneys, liver and lungs were removed, homogenized in sterile saline (hand-held glass tissue homogenizer) and plated onto Mycosel agar for cfu. The tissue homogenization does not cause measurable death of fungal elements (Poor, A. H. et al. 1981. Analysis of an in vivo model to study the interaction of host factors with *C. albicans*. Infect. Immun. 31:1104–1109).

As can be seen in Table 1, cfu from organs of mice that received immune serum were less in all organs with the most striking differences noted in the kidneys. These data suggest that immune serum contains factors that may protect mice against hematogenous disseminated candidiasis.

TABLE 1

Evidence that anti-adhesin serum transfers protection against disseminated candidiasis to naive mice.

| Organs | Colony forming units (cfu) (±SD of coefficient)/g tissue homogenate | | |
|---|---|---|---|
| | Immune Serum | Normal Serum | No Serum |
| Spleen | $0.6 \times 10^4 \pm 0.5$ | $1.5 \times 10^4 \pm 0.4$ | $1.3 \times 10^4 \pm 0.1$ |
| Kidneys | $2.1 \times 10^4 \pm 1.4$ | $5.2 \times 10^4 \pm 1.7$ | $4.2 \times 10^4 \pm 0.3$ |
| Liver | $1.5 \times 10^3 \pm 0.3$ | $3.1 \times 10^3 \pm 1.8$ | $2.5 \times 10^3 \pm 0.6$ |
| Lungs | $2.3 \times 10^2 \pm 0.4$ | $2.9 \times 10^2 \pm 0.6$ | $2.8 \times 10^2 \pm 0.4$ |

EXAMPLE 14

Measurement of antibody responses:

Mouse polyclonal anti-2ME extract caused agglutination of whole yeast cells. Latex beads coated with the 2ME extract as previously reported, (Li, R. K., et al. 1993. Chemical definition of an epitope/adhesin molecule on *C. albicans*. J. Biol. Chem. 268:18293–18299), agglutinate strongly in the presence of the polyclonal antisera, whereas no agglutination occurs in the presence of normal mouse serum (NMS), and agglutination of the 2ME extract-latex is blocked by addition of soluble 2ME extract. Latex agglutination titers of the various sera are determined by adding 25 µl of the 2ME latex conjugate, mixing by rotation for 2–5 min and determining the agglutination end-point.

An anti-adhesin ELISA assay was also developed. Because of its sensitivity and ability to simultaneously test many different samples, the ELISA will be especially useful in characterizing the predominant class of immunoglobulins produced in protective sera as indicated below. Coating microtiter plates with 2ME extract or Fr.II readily occurs in the presence of 0.06M carbonate buffer (pH 9.6); 3% BSA neutralizes non-specific binding. Confirmation of adhesin binding to the plates is accomplished by demonstrating specific reactivity with the adhesin-specific mAb 10G as detected by commercial secondary anti-mouse Ig-enzyme and substrate; showing that mAb 10G does not bind to the plates in the presence of soluble 10G antigen or 2ME extract; and, binding of an irrelevant mAb or NMS is low. It was found that 2ME extract-coated plates may be stored indefinitely at 20° C.

Tail vein blood from vaccinated mice was evaluated for antibody titers (anti-Ig) on a weekly basis during the five weeks of vaccinations-boosters. After that time titers will be determined every three weeks until antibody levels decline near background. Various classes/subclasses of antibodies in the antisera will also be titered by use of the ELISA assay. Commercially available enzyme-labeled antibodies specific for the various mouse Ig heavy chains will be used. This experiment will be of interest later if, for example, IgM anti-adhesins are found in high titer in mice that are protected, as opposed to $IgG_{2b}$ that might predominate in mice poorly protected.

EXAMPLE 15

Pools of mAbs specific for candidal adhesins are also used for passive transfer. Ascites fluid of each mAb and their concentrated Ig fractions obtained by use of an ABx HPLC preparative column are available. This column works very well for isolation of IgM and IgG classes of mAbs. Dr. Hazen provided the mAbs specific for hydrophobic adhesins of *C. albicans*.

Mice (initially BALB/c females) are given various doses of pools of mAbs against the various adhesins. The protocols chosen are roughly deduced from results obtained with polyclonal antiserum experiments. After establishing antibody titers, the animals are challenged with appropriate doses of *C. albicans* and organ cfu determined at various times after challenge. Control animals receive mAbs known to react with the cell surface of *C. albicans*, but have been shown not to react with adhesin sites (e.g., mAb 2B3.1). Mab H9 (Brawner, D. L., et al. 1984. Variability in expression of a cell surface determinant on *C. albicans* as evidenced by an agglutinating monoclonal antibody. Infect. Immun. 43:966–972; and Brawner, D. L., et al. 1986. Variability in expression of cell surface antigens of *C. albicans* during morphogenesis. Infect. Immun. 51:337–343) reacts with a candidal carbohydrate surface epitope not involved in adhesion events (our unpublished data).

Control mAbs (2B3.1 and H9) and our anti-adhesin mAb (mAb 10G) are of the IgM class. Isotype switching work can be performed as known in the art (Schlageter, A. M. et al. 1990. Opsonization of *Cryptococcus neoformans* by a family of isotype-switch variant antibodies specific for the capsular polysaccharide. Infect. Immun. 58:1914–1918) if required to provide specificity for monoclonal antibodies of the invention.

The number of different kinds of mAbs in the pooled mAb preparations are systematically dissected to determine the minimum number required for protection.

EXAMPLE 16

The effects of anti-adhesins on attachment phenomena was investigated. Sera from vaccinated mice inhibits the adhesins (2ME extract) from binding to splenic marginal zone tissue and the antiserum also prevents attachment of hydrophilic yeast cells to the spleen.

As Ig fractions of antisera and mAbs become available, approaches are used similar to those already applied in the ex vivo assay to test the effect of antisera (anti-sMB extract) on yeast cell adherence to the splenic marginal zone. The various polyclonal antisera and mAbs are selected based upon preliminary results. Their effects, either singly or in combination, on tissue adherence of hydrophilic and hydrophobic yeast cells, complement-coated yeast cells and adhesin-producing recombinant *C. albicans* strains are determined. The systems used for study and comparison include the ex vivo assay, the endothelial assay and the capillary shear-dependent adhesion assay. Intravital microscopy is used to follow yeast cell endothelial interactions within mice that have been vaccinated and in non-sensitized mice given polyclonal and mAbs. In all of these methods, careful consideration is given to appropriate controls. Depending on the experiment, non-binding yeasts such as *C. neoformans* or *S. cerevisiae* transformed with plasmid only are used as negative binding controls. NMS and isotype-matched irrelevant mAbs are used as negative controls for immune polyclonal antisera and mAbs, respectively. The detailed use of these various adherence techniques and data acquisition/evaluation methods are given in the respective proposal from each investigator and/or their publications.

The pathogenesis of hematogenous disseminated candidiasis appears to involve adhesion events between yeast cells of *C. albicans* and specific host tissues. Host antibodies specific for candidal adhesins alter the pathogenesis and may aid host survival. Candidal adhesins have been isolated that cause specific yeast cell adherence to mouse splenic marginal zone macrophages. These adhesins are part of the phosphomannoprotein (PMP) complex on the candidal cell surface. Vaccines made of solubilized adhesins encapsulated in liposomes provoke antibody responses in mice against the adhesins. Vaccinated animals have increased resistance against disseminated candidiasis, their serum neutralizes adhesin activity, prevents yeast cell attachment to the spleen and appears to transfer protection. Monoclonal antibodies (mAbs) against the PMP-derived adhesins are available from Dr. Cutler. The effects of polyclonal and mAbs on adherence interactions with various tissues are extensively evaluated by adherence assays.

The vaccine may be formulated in liposome formulations as set forth above. Additional formulations may be prepared as with formulations and adjuvants as known in the art (see Remingtons Pharmaceutical Sciences, 18th ed., Mack Publishing Co., 1990). Vaccines may include from 0.01 to 99.00% by weight adhesin composition. The vaccine of the present invention may, in a preferred embodiment, be formulated in an effective amount of about 0.5 g per human of 150 lbs.

EXAMPLE 17

Organisms, culture conditions and isolation of the adhesin fraction.

*C. albicans* serotypes A (strain 1) and B (strain A9) were used and previously characterized (8,20,21,49). *C. tropicalis* strain CT-4 is from Montanta State University stock collection and species identification was confirmed by API 20C Yeast Identification Strips (Analytab Products, Plainview, N.Y.). Stock cultures were stored and maintained as described (19,20) and grown to stationary phase in GYEP broth (19,20) at 37 C. The yeast cells were washed three times in sterile deionized water, suspended to the appropriate concentration in sterile Dulbecco's phosphate buffered saline (DPBS) (Sigma Chem. Co., St. Louis, Mo.), and used to challenge mice.

The PMC (referred to as the adhesin extract) was obtained in crude form, as before (19,20), by a b-mercaptoethanol extraction of the serotype A isolate of *C. albicans*. Less than 1 mg of this extract inhibited adherence of yeast cells to splenic and lymph node macrophages, hence, it contains the adhesins (17,20). Chemically, the extract is primarily mannan with about 3.5% protein. Following proteinase digestion, the protein content dropped to 0.47%, yet all adhesin activity was retained (20).

Liposome encapsulation of the adhesin extract.

The adhesin extract was encapsulated into multilamellar liposomes as described previously (11). Briefly, 200 μl of phosphatidylcholine (100 mg phosphatidylcholine/ml chloroform) and 30 μl of cholesterol (100 mg cholesterol/ml chloroform) (molar ratio of phosphatidylcholine/cholesterol at approximately 3.2:1) were combined into 10 ml of chloroform-methanol (1:1) in a 500 ml round bottom flask. The solution was dried as a thin film by rotary evaporation at 37 C. under reduced pressure. The film was dissolved in 10 ml of chloroform, evaporated again, dispersed at room temperature for 10 min in 5 ml DPBS containing 10 mg of the adhesin extract, allowed to stand for 2 h, sonicated for 3 min and held at room temperature for an additional 2 h. To separate non-liposome associated antigen from liposome encapsulated antigen, the preparation was sedimented by centrifugation at 1,000×g for 30 min. The pelleted liposomes were suspended in 5 ml DPBS, pelleted again and this process was repeated two more times. The liposome-encapsulated adhesin extract, referred to as L-adhesin, was finally suspended in 4 ml DPBS and stored at 4 C. under nitrogen for up to 2 weeks. The amount of adhesin extract within the L-adhesin was 178 mg/ml as determined by the phenol-sulfuric acid reaction (12). Control liposomes were prepared exactly as above, but buffer (DPBS) without adhesin extract was added during the preparation. These control liposomes are referred to as L-PBS.

Vaccination and challenge of mice.

In all experiments mice were used and housed in accordance with institutional regulations in an AAALAC certified animal facility. BALB/cByJ (Jackson Labs, Bar Harbor, Me.) female mice, 6–7 weeks old, received the initial vaccine and weekly booster immunizations. Each injection consisted of 0.2 ml of the liposome-adhesin complex (L-adhesin) administered intravenously (i.v.). Anti-adhesin titers in mouse sera were assessed by slide agglutination against latex beads coated with the adhesin extract. Adhesin coating was done as before (19,20,27). When the agglutinin titers reached 40 or more (usually by the 4th booster), the animals were challenged. Control mice received an equal volume and number of injections consisting of diluent (DPBS) only prior to challenge. The mice were challenged i.v. with viable yeast cells prepared to the appropriate concentration in 0.2 ml DPBS.

Treatment of polyclonal antiserum.

To characterize the nature of the protective factor(s) in antiserum, polyclonal antiserum was obtained and pooled from vaccinated mice. The serum fraction was either immediately stored at −20 C., heated at 56 C. for 30 min prior to use, or adsorbed five times with formalin killed washed *C. albicans* strain 1 yeast cells at a ratio of ten volumes antiserum to one volume DPBS-washed packed dead yeast cells.

The antiserum was also fractionated by passage through an ABx HPLC column (J. T. Baker, Phillipsburg, N.J.) as described (40) to obtain pools of various separated serum components, including a fraction which contained all of the agglutinin activity. Briefly, buffer A consisted of 25 mM MES (2-[N-Morpholino]ethanesulfonic acid) (Sigma), pH 5.2–5.8 and buffer B was 1M sodium acetate, pH7.0. One part of polyclonal antiserum was mixed with two parts buffer A and the mixture was loaded onto the ABx column with buffer A at a flow rate of 1.5 ml/min and each fraction was 40 drops. At ten minutes, the percent of buffer B was brought to 20, at 15 min buffer B was brought to 50%, at 20 min it was brought to 70% at 25 min it was brought to 100% and was retained at 100% until 55 min at which time the run was terminated. Each of the peaks detected by absorption at 280 nm was collected, dialyzed against at least 100 volumes of DPBS at 4 C. with a minimum of four changes of DPBS over a 36 h period, and each pooled fraction was concentrated by ultrafiltration (PM30 Diaflo Ultrafiltration membrane, Amicon Division, Beverly, Mass.). Each concentrated fraction was brought to approximately one-half of the original starting volume of antiserum applied to the column. Each was tested for the ability to agglutinate whole yeast cells and latex beads coated with the adhesin fraction.

Passive transfer experiments.

Normal mouse serum (control), polyclonal antisera, antisera heated at 56 C., *C. albicans*-adsorbed antisera and HPLC-fractionated polyclonal antisera were tested for their ability to transfer resistance against disseminated candidiasis to naive mice. For each condition, 7–8 week old female or male BALB/cByJ mice (Jackson Labs) were given 0.5 ml of the test serum intraperitoneally (i.p.), 4 h later they were given 0.2 ml i.v. of a suspension containing $2.5 \times 10^6$ yeasts/ml DPBS and 20 h later they were given i.p. another 0.2 ml of test serum. Forty-eight hours after challenge, candidal cfu/g kidney were determined as described below. In some experiments, passive transfer of immune serum and challenge with live yeast cells were done in 18–20 weeks old male SCID mice (BALB/cByJSmn-scid/J, Jackson Labs).

Isolation and characterization of monoclonal antibodies (mAbs).

Mice were immunized with whole yeast cells (4) or the L-adhesin (11) and two mAbs specific for yeast surface epitopes were isolated as before (4,11). MAbB6 has the same specificity as mAb C6 (6) and mAb B6.1 is specific for an epitope in the PMC of *C. albicans*.

The epitope specificity of mAb B6 differs from mAb B6.1 as evidenced by Ouchterlony lines of non-identity against candidal cell wall extracts. Both of the mAbs agglutinate *C. albicans* yeast cells and both are IgM as indicated by reactions with commercial Ig-heavy chain specific antibodies (Sigma).

The mAbs were produced in serum free medium, concentrated by ammonium sulfate precipitation, and suspended and diluted in DPBS to give identical agglutinin titers. The same strategy as described above for polyclonal antiserum was used to determine the ability of mAbs B6 and B6.1 to transfer protection.

In these experiments, the agglutinin titers of each mAb was diluted to 20 (approximately 220 mg/ml for mAb B6.1 and 290 mg/ml for mAb B6) before administration to the BALB/cByJ mice. In one experiment, mAb B6 was obtained from ascites fluid, adjusted to an agglutinin titer of 320 and compared to the effect of mAb B6.1 at a titer of 20.

Assessment of resistance/susceptibility to disseminated candidiasis.

To determine relative susceptibility or resistance to disseminated candidiasis, we used survival curves and/or colony forming units (cfu) per g kidney tissue in mice challenged i.v. with yeast form cells of *C. albicans*. For survival curves, groups of test and control animals consisted of a minimum of five mice per group. Survival differences between the groups were calculated for statistical significance by the Kolmogorov-Smirnov two sample test (9). The kidney is a target organ in experimental disseminated candidiasis, therefore, *C. albicans* cfu in kidney tissue may be used as an indicator of disease severity (28,43,46). The cfu determinations were done by homogenizing the kidneys with glass tissue homogenizers as described (43) except that the kidneys were homogenized in 1 ml DPBS and plated onto Mycosel agar (BBL Microbiology Systems, Becton Dickinson and Co., Cockeysville, Md.). Statistical significance of difference between test and control groups was determined by the Student t-test.

Vaccinated mice have increased survival rates.

Vaccinated mice showed more resistance to disseminated candidiasis than did control mice as indicated by an increase in mean survival times following challenge (Table 1). To demonstrate a requirement for liposome delivery, some animals were given i.v. an equivalent amount of adhesin extract (178 mg) in 0.2 ml DPBS, but without liposomes. The mean survival times of these animals did not differ from animals that received only DPBS (data not shown).

Serum from vaccinated mice transfers protection.

Figure 11A:
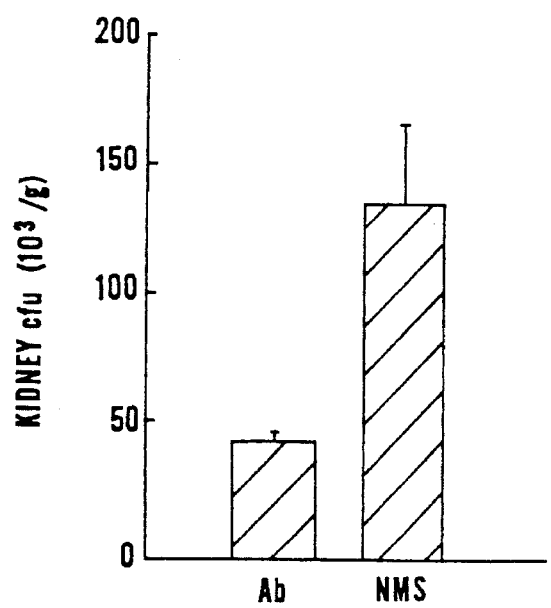
FIGS. 11A and 11B show pooled polyclonal antiserum from vaccinated mice protected both naive normal BALB/cByJ and SCID mice from disseminated disease.
Figure 11B:
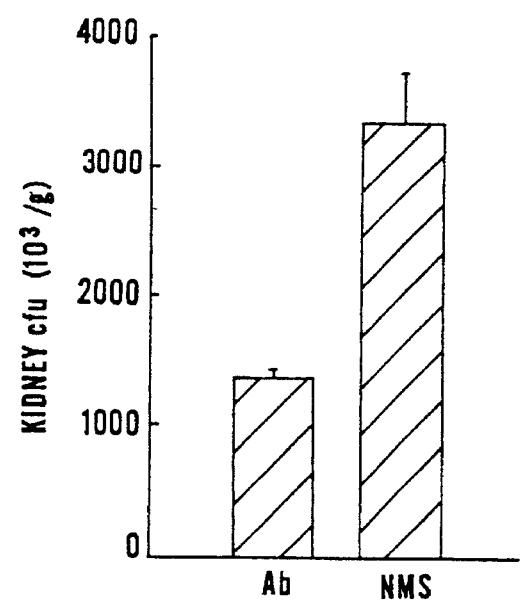

Pooled polyclonal antiserum from vaccinated mice protected both naive normal BALB/cByJ and SCID mice from disseminated disease (FIG. 11). Whereas heat treatment (56 C., 30 min) had no effect on the protective ability of the antiserum, adsorption with *C. albicans* yeast cells removed the activity.

To determine if the vaccine induces protection against both serotypes of *C. albicans* and against other Candida species, mice were passively given, as above, the antiserotype A polyclonal antiserum and challenged i.v. with either a serotype B strain of *C. albicans* ($5\times10^5$ yeast cells) or a strain of *C. tropicalis* ($1\times10^6$ yeast cells). Kidneys were removed 48 h later for cfu determinations. Antiserum-treated mice challenged with the serotype B strain had 11.3 ($\pm2.7$)$\times10^3$ cfu/g kidney tissue, while normal mouse serum (NMS)- treated mice (controls) had 41.4 ($\pm7.0$)$\times10^3$ cfu/g ($p<0.001$) ($\pm$are standard error values). Likewise, antiserum-treated mice challenged with *C. tropicalis* developed 145 ($\pm16$)$\times10^3$ cfu/g kidney as compared to 267 ($\pm34$)$\times10^3$ cfu/g for NMS-treated controls ($p<0.001$) ($\pm$are standard error values).

Two fractions from antiserum transfer protection.

Figure 12:
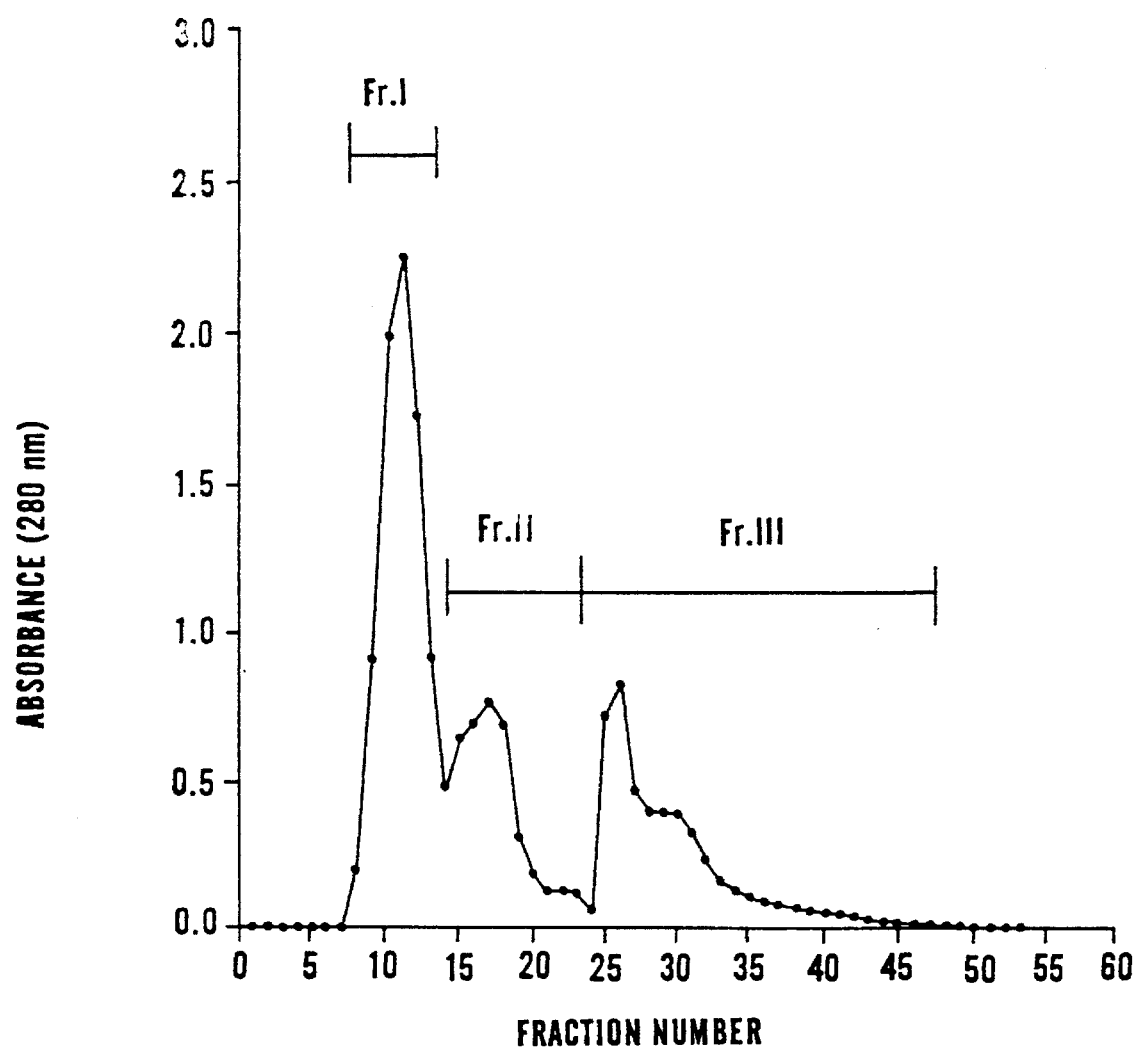
FIG. 12 shows antiserum separated by use of an ABx HPLC column yielded three major fractions, Fr.I, Fr.II, Fr.III.

Antiserum separated by use of an ABx HPLC column yielded three major fractions, Fr.I, Fr.II, Fr.III (FIG. 12). All of the detectable agglutinin activity was associated with Fr.III. Fr.III gave the strongest evidence for ability to transfer protection, but protective activity was also associated with Fr.II. That is, mice given either normal mouse serum (negative control), unfractionated polyclonal antiserum (positive control), Fr.I, Fr.II or Fr.III and challenged with *C. albicans* i.v. resulted in 109 ($\pm33.3$), 40.9 ($\pm2.3$), 93.2 ($\pm9.5$), 59.2 ($\pm11.4$) and 50.9 ($\pm9.7$)$\times10^3$ cfu/g kidney, respectively ($\pm$are standard error values). The differences were significant to $p<0.05$ when polyclonal antiserum, Fr.II or Fr.III were each compared to cfu/g tissue for animals treated with normal mouse serum. In these experiments, the total amount of protein received by each mouse was 22.4 mg of Fr.I, 3.8 mg of Fr.II and 22.6 mg of Fr.III. The antibody activity (agglutination titer) of Fr.III (22.6 mg) was the same as the agglutinin activity of unfractionated polyclonal antiserum.

MAb B6.1 transfers protection, but mAb B6 does not.

Figure 13A:
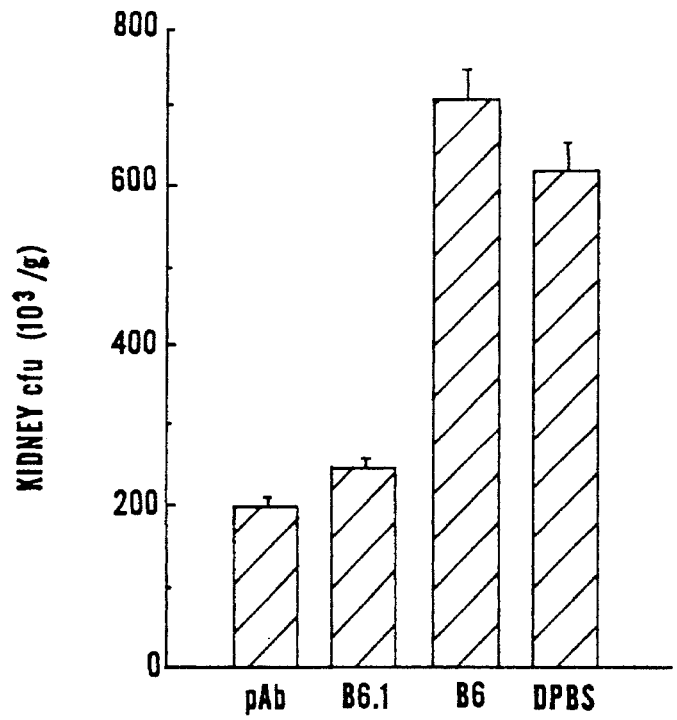
FIGS. 13A and 13B show that although both mAbs are strong agglutinins and are of the same class, only mAb B6.1 transferred protection against disseminated candidiasis to naive BALB/cByJ mice. This result was demonstrated by both cfu/g kidney counts (FIG. 13A) and by survival curve analysis (FIG. 13B).
Figure 13B:
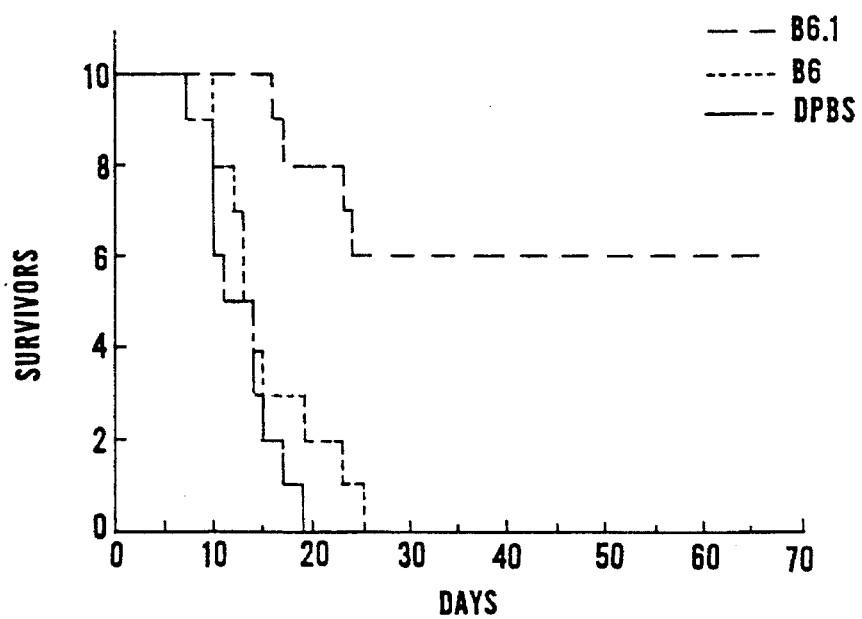
Figure 14:
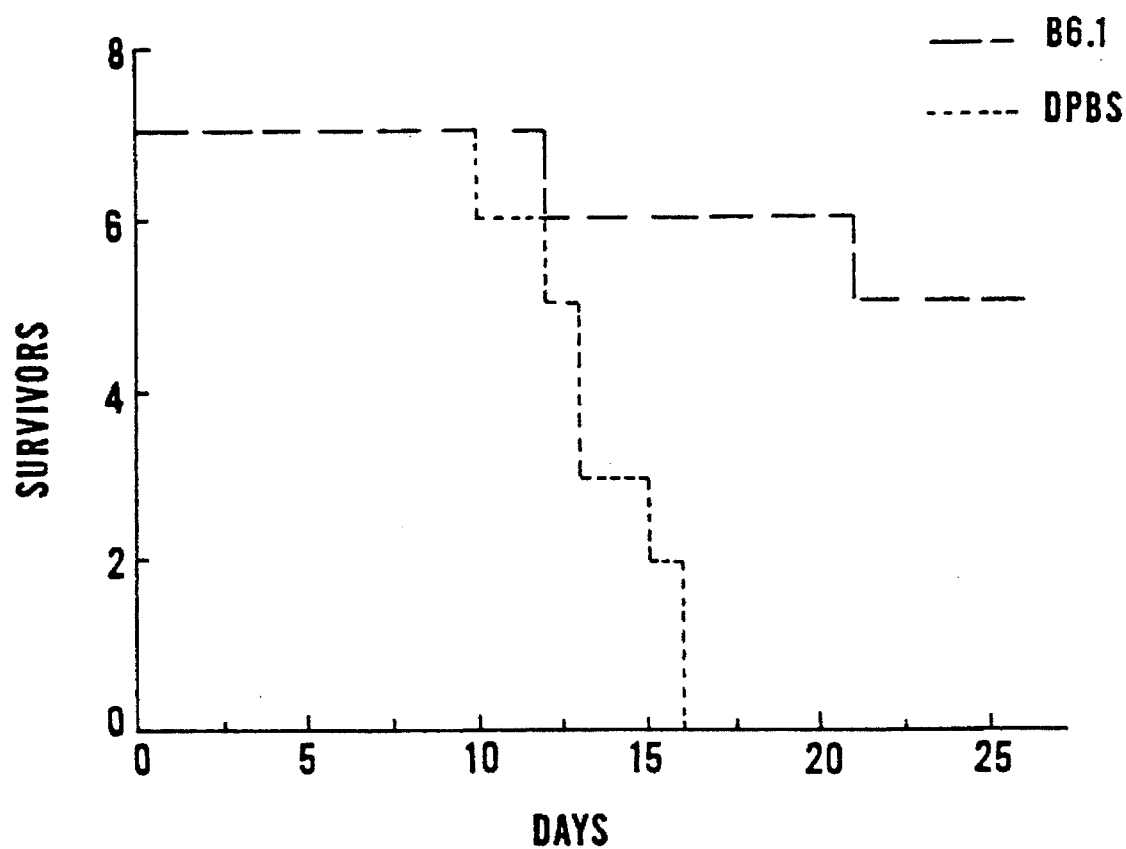
FIG. 14 shows SCID mice treated with mAb B6.1 survived significantly (p<0.01) longer than control mice.

Although both mAbs are strong agglutinins and are of the same class, only mAb B6.1 transferred protection against disseminated candidiasis to naive BALB/cByJ mice. This result was demonstrated by both cfu/g kidney counts (FIG. 13A) and by survival curve analysis (FIG. 13B). In these experiments, both mAbs were standardized to have the same agglutinin titers as indicated in the Materials and Methods. In one experiment, the titer of mAb B6 was increased to approximately 16 times that of mAb B6.1 and administered to mice in the volumes and schedules as indicated. Even though the agglutinin titers at day 2 after administration were 10 for animals that received mAb B6 and 2 for mice that received mAb B6.1, no protection was observed due to mAb B6 as compared to mice given DPBS prior to yeast cell challenge (data not shown). In the survival experiments, of ten BALB/cByJ mice treated with mAb B6.1, six survived the entire 67 day observation period, whereas all mAb B6 treated mice died by day 25 and all control (DPBS treated) mice died by day 19 (FIG. 13B). Likewise, SCID mice treated with mAb B6.1 survived significantly ($p<0.01$) longer than control mice (FIG. 14). In experiments on BALB/cByJ mice, the 67 day survivors were sacrificed and their kidneys and spleens were plated for candidal cfu. No cfu in splenic tissues were detected in any of the animals. However, the kidneys from two of the mice showed cfu development ($97.7\times10^3$/g and $207.7\times10^3$/g), whereas no cfu were detected in undiluted homogenates of kidneys from four of the mice.

This work provides strong evidence that antibodies specific for certain cell surface determinants on *C. albicans* aid the host in resistance against disseminated candidiasis. First, mice with enhanced resistance were those that were L-adhesin vaccinated and had agglutinin titers of 40–80. Second, mice vaccinated with only the adhesin extract developed low anti-adhesin titers (less than 5) and showed no enhanced resistance. Third, polyclonal antiserum from vaccinated mice protected naive normal BALB/cByJ and SCID mice from disseminated disease (FIG. 11). SCID mice, however, did not make antibodies or develop a protective response as a result of the vaccinations (data not shown). Fourth, heat treatment (56 C., 30 min) had no effect on the protective ability of the polyclonal antiserum, but adsorption with *C. albicans* removed the activity. Fifth, fractionation of the antiserum by an HPLC ABx column yielded a fraction that contained all of the agglutinin activity and this fraction transferred protection to naive animals. Sixth, mice that received mAb B6.1, which is specific for the adhesin extract and is a strong agglutinin of whole yeast cells, developed fewer cfu in their kidneys following challenge and both normal and SCID mice survived significantly longer than control animals (FIGS. 13 and 14). In this experiment (FIG. 13B), six out of ten of the treated BALB/cByJ animals survived the entire 67 day observation period and four out of six of the survivors appeared to be cured as evidenced by the lack of cfu recoverable from their spleen and kidneys.

The results also show that an antibody with specificity for a cell surface determinant of *C. albicans* may not necessarily protect animals against disseminated disease. These findings explain the variable results earlier workers have obtained regarding the role of antibodies in protection against disseminated candidiasis. Animals that received the agglutinating IgM mAb B6 were just as susceptible as controls to disseminated candidiasis, even when mAb B6 was given at about 16 times the titer of mAb B6.1 with resulting higher in vivo titers than in animals that received mAb B6.1. The inventors have also found two additional mAbs specific for surface determinants that also do not protect (unpublished data). These results support the hypothesis that antibodies of only certain specificities against *C. ablicans* are protective.

Strains of *C. ablicans* are either serotype A or B and both types can cause disseminated disease (41). In addition, there is an increasing number of candidiasis cases due to other candidal species such as *C. tropicalis* (26,32). The vaccine of the present invention induces in mice a response that also protects against disseminated disease due to a serotype B strain of *C. albicans* and against *C. tropicalis*. These data suggest that antiserum from vaccinated mice contains antibodies that are broadly protective.

The inventors have determined that mAb B6.1 also protects mice against serotype B and *C. tropicalis* strains. The explanation for the broad protection of polyclonal antiserum appears to involve antibodies with varying specificities, antibodies with specificity for the B6.1 epitope. Since it has been found that mAb B6.1 also protects SCID mice, neither T nor B cells appear to be involved in the protection.

Not being bound by any one theory, one possible mechanism is that antibodies in the mouse cause simple agglutination of the yeast cells which effectively reduces the number of independent infection units. This explanation does not seem likely because mAb B6 does not protect, but it is a strong agglutinin. In fact, it causes larger agglutinates at a given titer than mAb B6.1 (unpublished observations). In animals that received the mAbs, the agglutinin titers in the serum of mice that received mAbs B6 or B6.1 were essentially the same. The lower cfu in mAb B6.1-treated animals, but not mAb B6-treated mice, also militates against the argument that cfu are artificially reduced because of the presence of serum agglutinins. In addition, animals that passively received mAb B6.1 had enhanced survival as compared to mice that received mAb B6.

Two other possibilities are that mAb B6.1 alters adherence of yeast cells in vivo, and/or enhances phagocytosis of yeast cells by neutrophils and macrophages. The first possibility is under investigation. The mechanism would not involve Fc receptors on phagocytic cells because mAb B6.1 is an IgM. However, mAb B6.1 may promote complement opsonization more efficiently than the non-protective IgM agglutinin, mAb B6.

REFERENCES

1. Anttila, V. J., P. Ruutu, S. Bondestam, S. E. Jansson, S. Nordling, M. F'arkkil'a, A. Sivonen, M. Castren, and T. Ruutu. 1994. Hepatosplenic yeast infection in patients with acute leukemia: a diagnostic problem. Clin. Infect. Dis. 18:979–981.
2. Banerjee, U., L. N. Mohapatra, and R. Kumar. 1984. Role of antibody in defence against murine candidosis. Indian J. Med. Res. 79:760–765.
3. Berenguer, J., M. Buck, F. Witebsky, F. Stock, P. A. Pizzo, and T. J. Walsh. 1993. Lysis-centrifugation blood cultures in the detection of tissue-proven invasive candidiasis. Diagn. Microbiol. Infect. Dis. 17:103–109.
4. Brawner, D. L. and J. E. Cutler. 1984. Variability in expression of a cell surface determinant on *C. ablicans* as evidenced by an agglutinating monoclonal antibody. Infect. Immun. 43:966–972.
5. Brawner, D. L. and J. E. Cutler. 1986. Variability in expression of cell surface antigens of *C. ablicans* during morphogenesis. Infect. Immun. 51:337–343.
6. Brawner, D. L. and J. E. Cutler. 1986. Ultrastructural and biochemical studies of two dynamically expressed cell surface determinants on *C. ablicans*. Infect. Immun. 51:327–336.
7. Brawner, D. L. and J. E. Cutler. 1987. Cell surface and intracellular expression of two *C. ablicans* antigens during in vitro and in vivo growth. Microbial Pathogen. 2:249–257.
8. Brawner, D. L. and J. E. Cutler. 1989. Oral *C. albicans* isolates from nonhospitalized normal carriers, immunocompetent hospitalized patients, and immunocompromised patients with or without acquired immunodeficiency syndrome. J. Clin. Microbiol. 27:1335–1341.
9. Campbell, R. C. 1967. The Kolmogorov-Smirnov one-sample test, p. 157–159. In R. C. Campbell (ed.), Statistics for biologists. University Press, Cambridge.
10. Critchley, I. A. and L. J. Douglas. 1987. Isolation and partial characterization of an adhesin from *C. albicans*. J. Gen. Microbiol. 133:629–636.
11. Cutler, J. E., Y. Han, and R. K. Li. 1994. Production of monoclonal antibodies against mannan determinants of *C. ablicans*, B. Maresca and G. S. Kobayashi (eds.). p. 197–206, In Molecular Biology of Pathogenic Fungi: A Laboratory Manual. Telos Press, New York. p. 197–206.
12. Dubois, M., K. A. Gillis, J. K. Hamilton, P. A. Rebers, and F. Smith. 1956. Colorimetric method for determination of sugars and related substances. Analyt. Chem. 28:350–356.
13. Filler, S. G., B. O. Ibe, A. S. Ibrahim, M. A. Ghannoum, J. U. Raj, and J. E. Edwards. 1994. Mechanisms by which *C. albicans* induces endothelial cell prostaglandin synthesis. Infect. Immun. 62:1064–1069.
14. Fruit, J., J. C. Cailliez, F. C. Odds, and D. Poulain. 1990. Expression of an epitope by surface glycoproteins of *C. ablicans*. Variability among species, strains and yeast cells of the genus Candida. J. Med. Vet. Mycol. 28:241–252.
15. Garner, R. and J. E. Domer. 1994. Lack of effect of *C. albicans* mannan on development of protective immune responses in experimental murine candidiasis. Infect. Immun. 62:738–741.
16. Giger, D. K., J. E. Domer, S. A. Moser, and J. T. McQuitty. 1978. Experimental murine candidiasis: pathological and immune responses in T-lymphocyte-depleted mice. Infect. Immun. 21:729–737.
17. Han, Y., N. van Rooijen, and J. E. Cutler. 1993. Binding of *C. albicans* yeast cells to mouse popliteal lymph node tissue is mediated by macrophages. Infect. Immun. 61:3244–3249.
18. Hazen, K. C., D. L. Brawner, M. H. Riesselman, M. A. Jutila, and J. E. Cutler. 1991. Differential adherence of hydrophobic and hydrophilic *C. albicans* yeast cells to mouse tissues. Infect. Immun. 59:907–912.
19. Kanbe, T. and J. E. Cutler. 1994. Evidence for adhesin activity in the acid-stable moiety of the phosphomannoprotein complex of *C. albicans*. Infect. Immun. 62:1662.–1668.
20. Kanbe, T., Y. Han, B. Redgrave, M. H. Riesselman, and J. E. Cutler. 1993. Evidence that mannans of *C. albicans* are responsible for adherence of yeast forms to spleen and lymph node tissue. Infect. Immun. 61:2578–2584.
21. Kanbe, T., M. A. Jutila, and J. E. Cutler. 1992. Evidence that *C. albicans* binds via a unique adhesion system on phagocytic cells in the marginal zone of the mouse spleen. Infect. Immun. 60:1972–1978.
22. Kanbe, T., R. K. Li, E. Wadsworth, R. A. Calderone, and J. E. Cutler. 1991. Evidence for expression of C3d receptor of *C. albicans* in vitro and in vivo by immunofluorescence and immunoelectron microscopy. Infect. Immun. 59:1832–1838.

23. Kobayashi, H., N. Shibata, M. Nakada, S. Chaki, K. Mizugami, Y. Ohkubo, and S. Suzuki. 1990. Structural study of cell wall phosphomannan of *C. albicans* NIH B-792 (serotype B) strain, with special reference to 1H and 13C NMO analyses of acid-labile oligomannosyl residues. Arch. Biochem. Biophys. 278:195–204.

24. Komshian, S. V., A. K. Uwaydah, J. D. Sobel, and L. R. Crane. 1989. Fungemia caused by Candida species and *Torulopsis glabrata* in the hospitalized patient: frequency, characteristics, and evaluation of factors influencing outcome. Rev. Infect. Dis. 11:379–390.

25. LaForce, F. M., D. M. Mills, K. Iverson, R. Cousins, and E. D. Everett. 1975. Inhibition of leukocyte candidacidal activity by serum from patients with disseminated candidiasis. J. Lab. Clin. Med. 86:657–666.

26. Lehrer, N., E. Segal, H. Lis, and Y. Gov. 1988. Effect of *C. albicans* cell wall components on the adhesion of the fungus to human and murine vaginal mucosa. Mycopathologia 102:115–121.

27. Li, R. K. and J. E. Cutler. 1993. Chemical definition of an epitope/adhesin molecule on *C. albicans*. J. Biol. Chem. 268:18293–18299.

28. Louria, D. B., R. G. Brayton, and G. Finkel. 1963. Studies on the pathogenesis of experimental *C. albicans* infections in mice. Sabouraudia 2:271–283.

29. Martinez, J. P., M. L. Gil, M. Casanova, J. L. Lopez-Ribot, J. G. De Lomas, and R. Sentandreu. 1990. Wall mannoproteins in cells from colonial phenotypic variants of *C. albicans*. J. Gen. Microbiol. 136:2421–2432.

30. Matthews, R. and J. Burnie. 1992. Acquired immunity to systemic candidiasis in immunodeficient mice: role of antibody to heat-shock protein 90. J. Infect. Dis. 166:1193–1194.

31. Matthews, R. C., J. P. Burnie, D. Howat, T. Rowland and F. Walton. 1991. Autoantibody to heat-shock protein 90 can mediate protection against systemic candidosis. Immunol. 74:20–24.

32. Meunier, F., M. Aoun, and N. Bitar. 1992. Candidemia in immunocompromised patients. Clin. Infect. Dis. 14 (Suppl 1):S120–S125.

33. Miyakawa, Y., T. Kuribayashi, K. Kagaya, and M. Suzuki. 1992. Role of specific determinants in mannan of *C. albicans* serotype A in adherence to human buccal epithelial cells. Infect. Immun. 60:2493–2499.

34. Molinari, A., M. J. Gomez, P. Crateri, A. Torosantucci, A. Cassone, and G. Arancia. 1993. Differential cell surface expression of mannoprotein epitopes in yeast and mycelial forms of *C. albicans*. Eur. J. Cell Biol. 60:146–153.

35. Mourad, S. and L. Friedman. 1961. Active immunization of mice against *C. albicans*. Proc. Soc. Exp. Biol. Med. 106:570–572.

36. Mourad, S. and L. Friedman. 1968. Passive immunization of mice against *C. albicans*. Sabouraudia 6:103–105.

37. Mukherjee, J., M. D. Scharff, and A. Casadevall. 1994. *Cryptococcus neoformans* infection can elicit protective antibodies in mice. Can. J. Microbiol. 40:888–892.

38. Mukherjee, J., L. Zuckier, M. D. Scharff, and A. Casadevall. 1994. Therapeutic efficacy of monoclonal antibodies to *Cryptococcus neoformans* glucuronoxylomannan alone and in combination with amphotericin B. Antimicrob. Agents Chemother. 38:580–587.

39. Mukherjee, S., S. Lee, J. Mukherjee, M. D. Scharff, and A. Casadevall. 1994. Monoclonal antibodies to *Cryptococcus neoformans* capsular polysaccharide modify the course of intravenous infection in mice. Infect. Immun. 62:1079.–1088.

40. Nau, D. R. 1986. A unique chromatographic matrix for rapid antibody purification. BioChromatography 1:82–94.

41. Odds, F. C. 1988. Candida and candidosis. Bailliere Tindall, London.

42. Pearsall, N. N., B. L. Adams, and R. Bunni. 1978. Immunologic responses to *C. albicans*. III. Effects of passive transfer of lymphoid cells or serum on murine candidiasis. J. Immunol. 120:1176–1180.

43. Qian, Q., M. A. Jutila, N. van Rooijen, and J. E. Cutler. 1994. Elimination of mouse splenic macrophages correlates with increased susceptibility to experimental disseminated candidiasis. J. Immunol. 152:5000–5008.

44. Reboli, A. C. 1993. Diagnosis of invasive candidiasis by a dot immunobinding assay for Candida antigen detection. J. Clin. Microbiol. 31:518–523.

45. Schaberg, D. R., D. H. Culver, and R. P. Gayner. 1991. Major trends in the microbial etiology of nosocomial infection. Am. J. Med. 16:72S–75S.

46. Sieck, T. G., M. A. Moors, H. R. Buckley, and K. J. Blank. 1993. Protection against murine disseminated candidiasis mediated by a *C. albicans*-specific T-cell line. Infect. Immun. 61:3540–3543.

47. Tronchin, G., J. P. Bouchara, V. Annaix, R. Robert, and J. M. Senet. 1991. Fungal cell adhesion molecules in *C. albicans*. Eur. J. Epidemiol. 7:23–33.

48. Walker, S. M. and S. J. Urbaniak. 1980. A serum-dependent defect of neutrophil function in chronic mucocutaneous candidiasis. J. Clin. Pathol. 33:370–372.

49. Whelan, W. L., J. M. Delga, E. Wadsworth, T. J. Walsh, K. J. Kwon-Chung, R. Calderone, and P. N. Lipke. 1990. Isolation and characterization of cell surface mutants of *C. albicans*. Infect. Immun. 58:1552–1557.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All publications and patents cited herein are hereby incorporated by reference in their entireties.

We claim:

1. A vaccine for the treatment of candidiasis comprising a composition of a pharmaceutically effective amount of adhesion molecules of *Candidia albicans* and a pharmaceutically acceptable carrier to elicit an immune response, wherein the adhesion molecules are isolated phosphomannoprotein cell wall complexes and the pharmaceutically acceptable carrier comprises a liposome.

2. The vaccine of claim 1, wherein said candidiasis is hematogenous disseminated candidiasis.

3. The vaccine of claim 1, wherein said liposome comprises cholesterol, phosphatidylcholine or mixtures thereof.

4. A method for immunization against candidiasis comprising administering the composition of claim 1 to a patient in need of said treatment.

5. A pharmaceutical composition to elicit an immune response to *C. albicans* comprising a composition of a pharmaceutically effective amount of adhesion molecules of *C. albicans* and a pharmaceutically acceptable carrier, wherein the adhesion molecules are isolated phosphomannoprotein cell wall complexes and the pharmaceutically acceptable carrier comprises a liposome.

* * * * *